(12) United States Patent
Dobrokhotov et al.

(10) Patent No.: US 10,802,008 B2
(45) Date of Patent: Oct. 13, 2020

(54) BIMETAL DOPED-METAL OXIDE-BASED CHEMICAL SENSORS

(71) Applicant: VAON, LLC, Bowling Green, KY (US)

(72) Inventors: Vladimir Dobrokhotov, Bowling Green, KY (US); Alexander Larin, Bowling Green, KY (US)

(73) Assignee: VAON, LLC, Bowling Green, KY (US)

( * ) Notice: Subject to any disclaimer, the term of this patent is extended or adjusted under 35 U.S.C. 154(b) by 160 days.

(21) Appl. No.: 15/907,410

(22) Filed: Feb. 28, 2018

(65) Prior Publication Data

US 2019/0004020 A1   Jan. 3, 2019

Related U.S. Application Data

(60) Provisional application No. 62/464,629, filed on Feb. 28, 2017.

(51) Int. Cl.
| | | |
|---|---|---|
| *G01N 33/00* | (2006.01) | |
| *G01N 25/34* | (2006.01) | |
| *G01N 27/12* | (2006.01) | |
| *G01N 1/22* | (2006.01) | |

(52) U.S. Cl.
CPC .......... *G01N 33/0031* (2013.01); *G01N 1/22* (2013.01); *G01N 25/34* (2013.01); *G01N 27/12* (2013.01); *G01N 27/128* (2013.01); *G01N 33/00* (2013.01); *G01N 33/0047* (2013.01); *G01N 2033/0019* (2013.01)

(58) Field of Classification Search
CPC .............. G01N 33/0031; G01N 33/00; G01N 33/0047; G01N 25/34; G01N 27/128; G01N 27/12; G01N 1/22; G01N 2033/0019
See application file for complete search history.

(56) References Cited

U.S. PATENT DOCUMENTS

| | | |
|---|---|---|
| 4,238,758 A | 12/1980 | Suzuki |
| 4,338,281 A | 7/1982 | Treitinger et al. |
| 4,399,684 A | 8/1983 | Advani et al. |
| 4,453,151 A | 6/1984 | Leary et al. |
| 4,542,640 A | 9/1985 | Clifford |
| 4,847,783 A | 7/1989 | Grace et al. |
| 5,250,170 A | 10/1993 | Yagawara et al. |
| 5,605,612 A | 2/1997 | Park et al. |

(Continued)

FOREIGN PATENT DOCUMENTS

| | | |
|---|---|---|
| GB | 2522294 A | 6/2016 |
| WO | 96/01992 | 1/1996 |

(Continued)

OTHER PUBLICATIONS

PCT/US18/20146 Written Opinion, dated Jun. 28, 2018 (corresponding PCT application).

(Continued)

*Primary Examiner* — Nathaniel T Woodward
(74) *Attorney, Agent, or Firm* — 21st Century IP LLP; Kelly Hollowell

(57) ABSTRACT

The present invention generally relates to bimetal-doped, metal oxide-based sensors and platforms and integrated chemical sensors incorporating the same, methods of making the same, and methods of using the same.

20 Claims, 18 Drawing Sheets

(56) References Cited

U.S. PATENT DOCUMENTS

| | | | |
|---|---|---|---|
| 5,783,154 | A | 7/1998 | Althainz et al. |
| 6,235,243 | B1 | 5/2001 | Fleischer et al. |
| 7,406,856 | B2 | 8/2008 | Bottner et al. |
| 8,669,131 | B1 | 3/2014 | Smith et al. |
| 2003/0045017 | A1 | 3/2003 | Kubena |
| 2004/0223884 | A1* | 11/2004 | Chen ............... G01N 29/036 422/88 |
| 2006/0185420 | A1 | 8/2006 | Nakagawa et al. |
| 2006/0196248 | A1 | 9/2006 | Nakano et al. |
| 2009/0148347 | A1 | 6/2009 | Lee et al. |
| 2009/0159447 | A1 | 6/2009 | Cui et al. |
| 2013/0140064 | A1 | 6/2013 | Burberry et al. |
| 2014/0138259 | A1 | 5/2014 | Mickelson et al. |
| 2014/0217478 | A1* | 8/2014 | Rothberg ............ B81B 3/0021 257/254 |
| 2015/0118111 | A1* | 4/2015 | Samarao ............ G01N 27/227 422/90 |
| 2016/0346762 | A1* | 12/2016 | Qu ..................... B01J 37/10 |
| 2016/0346763 | A1* | 12/2016 | Wahab ............... B01J 21/063 |
| 2017/0276627 | A1 | 9/2017 | Dobrokhotov et al. |
| 2018/0017516 | A1 | 1/2018 | Dobrokhotov et al. |

FOREIGN PATENT DOCUMENTS

| | | |
|---|---|---|
| WO | 03/062196 A2 | 7/2003 |
| WO | 2003062196 * | 7/2003 |

OTHER PUBLICATIONS

U.S. Appl. No. 15/466,712, filed Dec. 13, 2016.
U.S. Appl. No. 15/649,602, filed Jul. 13, 2017.
The Karlsruhe Micro Nose, KAMINA, Application Note: 31052, 2008.
Goschnick, J. et al., Condition Monitoring for Intelligent Household Appliances, Sensors in Household Appliances 2002, 5, 52-68.
The Karlsruhe Micronose KAMINA: Novel technology for intelligent systems (brochure).
Arnold, C. et al., Air Quality Monitoring and Fire Detection with the Karlsruhe Electronic Micronose Kamina, IEEE Sensor Journal, Aug. 2001, 1-22.
Chen, D. et al., Core-shell Au@Pd nanoparticles with enhanced catalytic activity for oxygen reduction reaction via core-shell Au@Ag/Pd constructions. Sci. Rep. 5, 11949; doi: 10.1038/srep11949 (2015).
Cao, K., et al., Controlled Synthesis of Pd/Pt Core Shell Nanoparticles Using Area-selective Atomic Layer Deposition. Sci. Rep. 5, 8470; DOI:10.1038/srep08470 (2015).
Larin, A. et al., Hybrid $SnO_2/TiO_2$ Nanocomposites for Selective Detection of Ultra-Low Hydrogen Sulfide Concentrations in Complex Backgrounds 2016, 16, 1373.

* cited by examiner

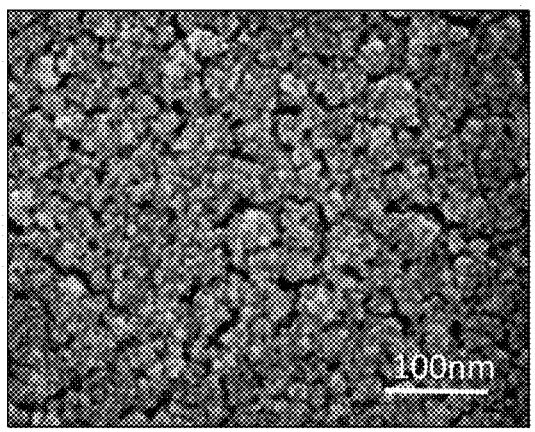 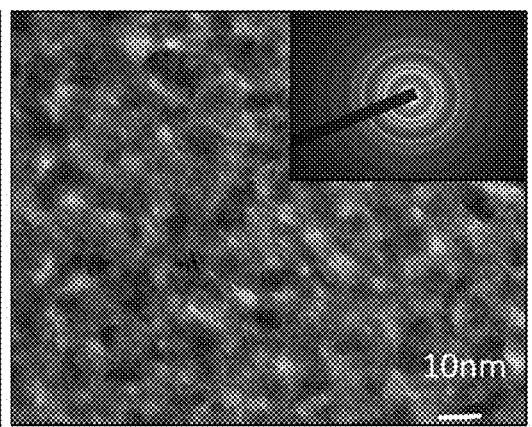
FIG. 2A  FIG. 2B
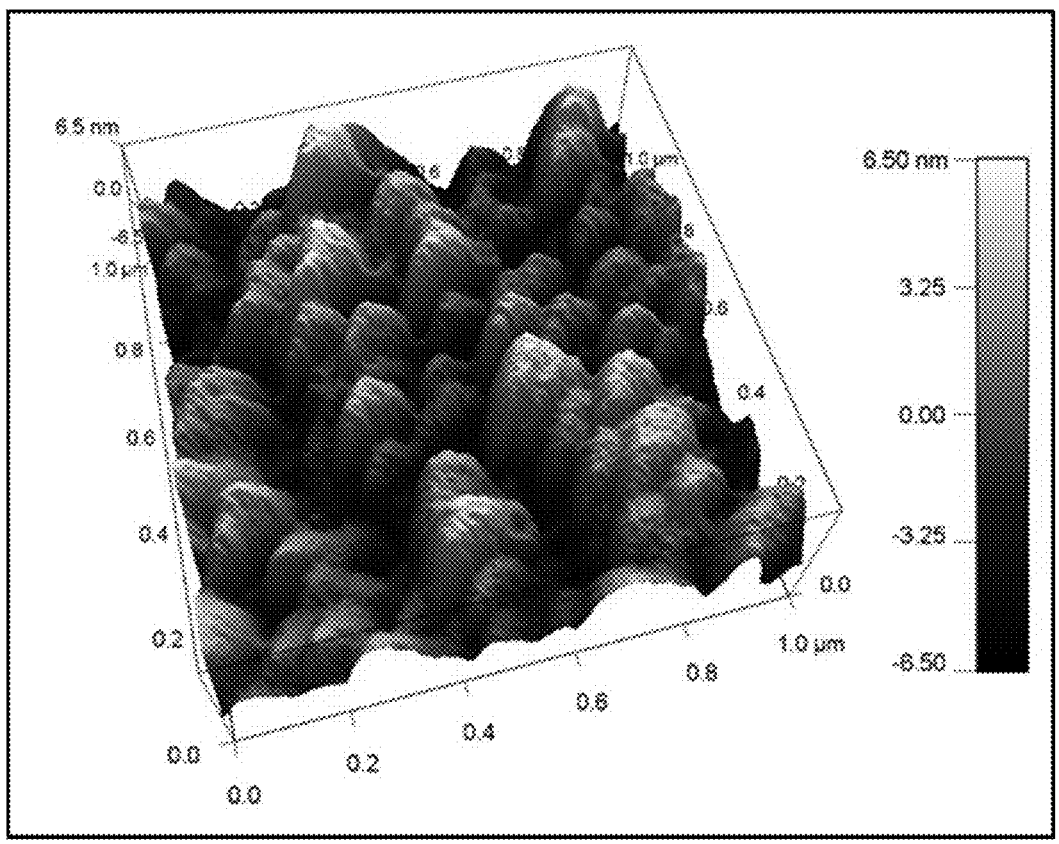
FIG. 2C

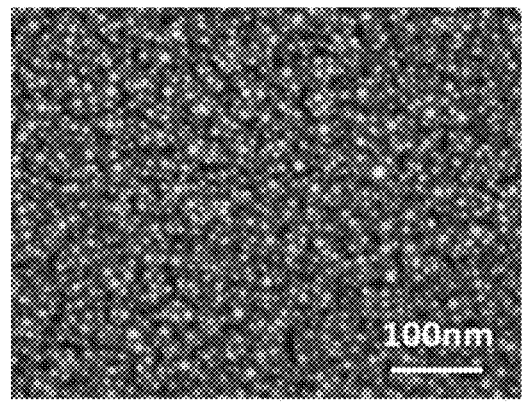
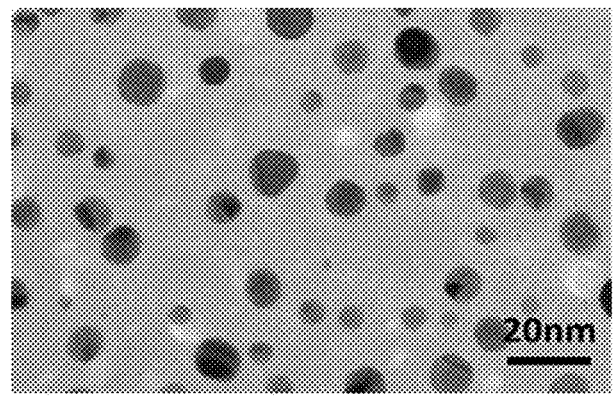
FIG. 4A  FIG. 4B
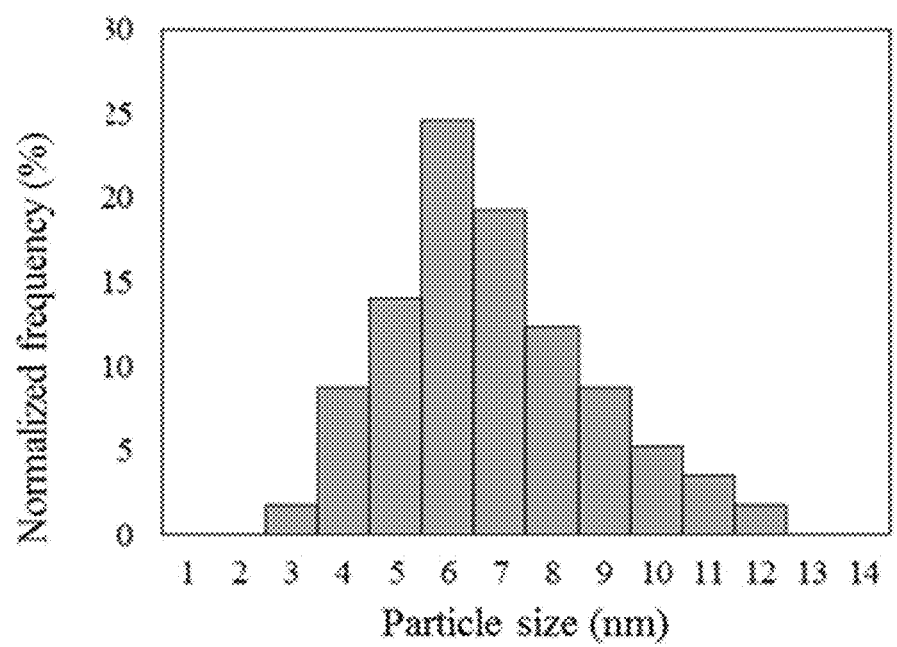
FIG. 4C

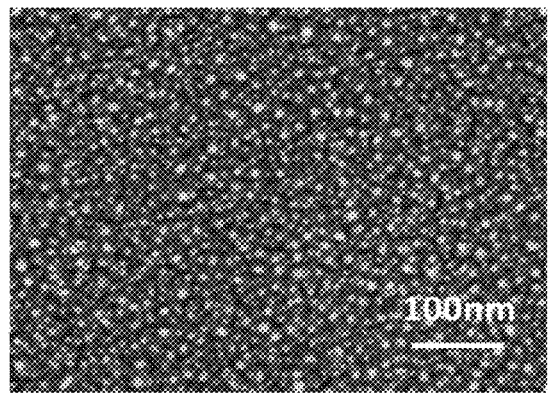
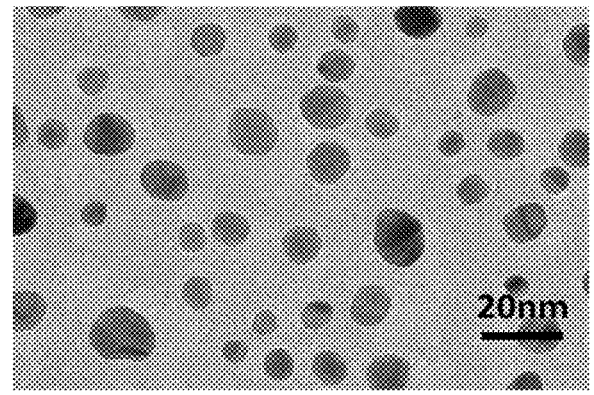
FIG. 4G　　　　　　　　　FIG. 4H
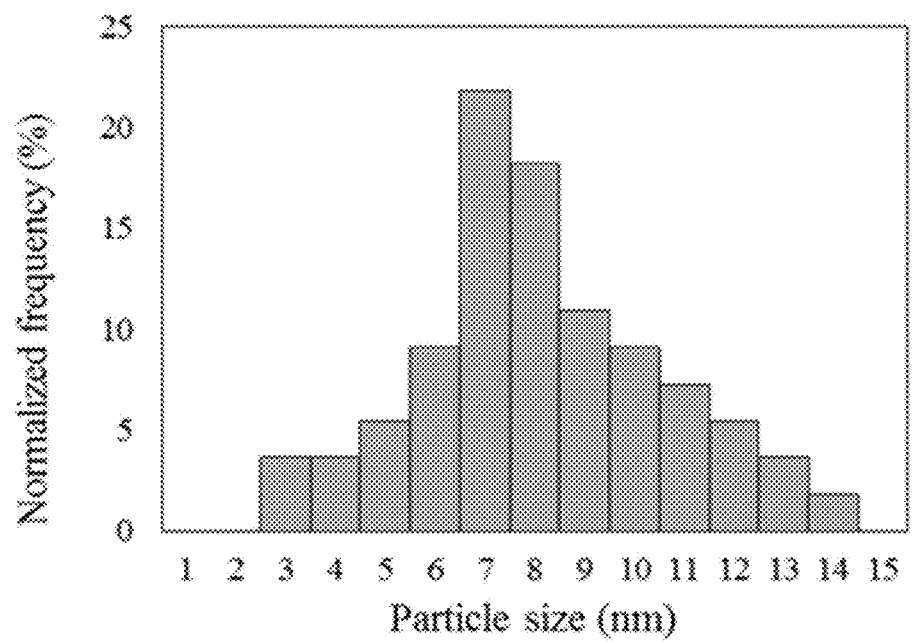
FIG. 4I

BIMETAL DOPED-METAL OXIDE-BASED CHEMICAL SENSORS

FIELD OF THE INVENTION

The present invention generally relates to bimetal-doped, metal oxide-based gas sensors and platforms and devices incorporating the same.

BACKGROUND OF THE INVENTION

Indoor air pollution by volatile organic compounds (VOC's) and its impact on human health has become a global issue in a modern world (Refs. 1-4). People typically spend most of their time indoors: in offices, vehicles, stores, at home etc. Modern industrial materials such as resins, paints, adhesives are broadly used in construction and interior design. At the same time, these materials contain a wide variety of VOCs. Recent studies have demonstrated the importance of understanding the sources of pollution and their regular monitoring because of high impact on human health (Ref 5). Among VOCs, BTEX (benzene, toluene, ethylbenzene and xylene) is the one of the major concerns (Ref 6). Even a small concentration of BTEX compounds has a significant negative impact on human health. Benzene is the most dangerous of the BTEX chemicals due to its high carcinogenicity (Ref 7). The indoor safety limit of benzene in the United States is in the range of 2.6-5 µg/m$^3$ (0.64-1.6 ppb) (Ref 8), which is similar to established indoor thresholds in Australia and Europe (Refs 9 and 10, respectively).

Numerous techniques have been developed to determine BTEX concentration in indoor air. Gas chromatography (GC) in combination with a variety of detectors, such as mass spectrometry (MS), flame ionization detector (FID), photo ionization detector (PID), pulse discharge detector (PDD) and thermal conductivity detector (TCD), together with IR and UV spectroscopy are the most commonly applied technique for monitoring BTEX compounds in the indoor air (Refs 11-18). The most popular GC detectors such as MS, FID, and PID have several advantages such as high sensitivity over an ultra-low concentration range (<1 ppb) in combination with high accuracy and selectivity (Refs 11, 17, and 19-21). However, a classical GC with standard sensors (FID, PID, and etc.) cannot be used for real-time field monitoring due to bulky size, heavy weight, special carrier gases requirement and high maintenance.

In order to overcome those problems, some portable miniaturized GCs with various kinds of detectors have been recently reported (see Table 1). Some portable GCs have been equipped with mini PIDs, micro FIDs (FID), on chip thermal conductivity detectors (pSC-TCD), and surface acoustic wave arrays (SAW) detector which were developed specifically for real time analysis (Refs 22-27). These new sensors demonstrated high sensitivity and selectivity toward VOCs at sub-ppb levels in combination with compact size and low power consumption. However, the major drawback of portable gas analyzers, e.g., special carrier gases, still has not been resolved.

TABLE 1

Major characteristics of some portable GCs for real time, portable field analysis of gas samples with different types of detectors.

| Detector | Carrier gas and flow rate (mL min$^{-1}$) | Sampling technique and injecting volume (mL) | Detection limit (LOD) VOCs (ppb) | One cycle analysis (min) | Ref |
|---|---|---|---|---|---|
| µFID | Oxyhydrogen (35) | N/A | VOS's (100) | N/A | 22 |
| mini PID | N$_2$/H$_2$ (2.5-3.5) | 6 port valve (0.2) | Benzene (<1) | 10 | 23 |
| µSC-TCD | He (1-5) | Pre-concentrator (10) | Benzene (<100) | 14.5 | 24 |
| SAW | He (1-5) | 6-port valve + Pre-concentrator (30) | Benzene (<1) | 1.3 | 26 |
| MIP-T | filtered ambient air (8) | 3-way valve Online sampling | Benzene (10000) | 4 | 30 |
| Metal Oxide MEMS sensor array (MOX) | filtered ambient air (15) | 3-way valve + Pre-concentrator (2700) | Benzene (0.1) | 60 | 31 |

Currently, novel types of sensors, such as surface modified Quartz Crystal Micro-balance system (QCM), miniaturized molecularly imprinted polymers quartz crystal tuning forks (MIP-TF) and novel metal oxide sensors have been investigated as detectors for the real time portable gas analysis (Refs 28-31). The weight, size and power consumption of miniaturized GC with the novel sensors has been drastically decreased, making them suitable for the field analysis. However, the sensitivity of such sensors without a long pre-concentration procedure is in the range of hundreds of parts per billion (ppb) to tens parts per million (ppm), makes it difficult to use those sensors for online indoor air quality monitoring, where acceptable threshold values for BTEX components are in the sub-ppb range.

In view of the above, it would be advantageous to develop new chemical sensors and devices using the same that address at least some of the above-noted drawbacks.

SUMMARY OF THE INVENTION

In an aspect, the present invention provides novel, bimetal-doped, metal oxide-based chemical sensors.

In another aspect, the present invention provides novel, bimetal-doped, metal oxide-based chemical sensor platforms.

In another aspect, the present invention provides novel devices comprising the sensors and/or chemical platforms.

These and other aspects, which will become apparent during the following detailed description, have been achieved by the inventors' discovery of new bimetal-doped, metal oxide-based chemical sensors.

BRIEF DESCRIPTION OF THE DRAWINGS

FIGS. 2A-C show SEM (FIG. 2A), TEM (FIG. 2B) and AFM (FIG. 2C) imaging of a $SnO_2$ thin film.

FIGS. 4A-H provide SEM imaging (FIG. 4A (S1), FIG. 4D (S2), and FIG. 4G (S3)), TEM imaging (FIG. 4B (S1), FIG. 4E (S2), and FIG. 4h (S3)), and nanoparticle size distribution analysis (FIG. 4C (S1), FIG. 4F (S2) and FIG. 4I (S3)) of the sensors S1-S3.

(FIG. 7C).

DETAILED DESCRIPTION OF THE INVENTION

Figure 1A:
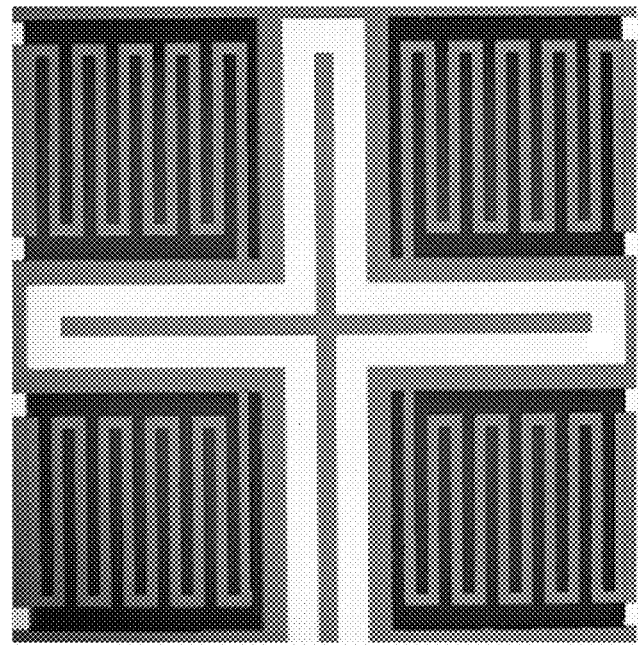
FIGS. 1A-C: shows the outline of the suspended membrane with four pairs of contacts and a cross-shaped heating element (FIG. 1A), a multi-sensory platform connected to the TO package (FIG. 1B), and a COMSOL™ simulation of the detector's temperature distribution (FIG. 1C).

In an aspect, the present invention provides a novel chemical sensor, comprising:
(a) an oxidized silicon membrane, comprising a silicon (Si) layer and a silicon oxide ($SiO_2$) layer, wherein the $SiO_2$ layer is located on top of the silicon layer and, comprises: a sensor area;
(b) a heating element in contact with the $SiO_2$ layer and located near at least one edge of the sensor area;
(c) a pair of electrical leads in contact with the $SiO_2$ layer and at least partly located on the sensor area; and,
(d) a metal oxide layer located on the sensor area and in contact with at least a part of the pair of electrical leads and the $SiO_2$ layer; and,
(e) a bimetal layer in contact with the metal oxide layer and comprising: Au and Pd.

In another aspect, the present invention provides a novel chemical sensor, comprising:
(a) an oxidized silicon membrane, comprising a silicon (Si) layer and a silicon oxide ($SiO_2$) layer, wherein the $SiO_2$ layer is located on top of the silicon layer and, comprises: a sensor area;
(b) a heating element in contact with the $SiO_2$ layer and located near at least one edge of the sensor area;
(c) a pair of electrical leads in contact with the $SiO_2$ layer and at least partly located on the sensor area; and,
(d) a metal oxide layer located on the sensor area and in contact with at least a part of the pair of electrical leads and the $SiO_2$ layer; and,
(e) a bimetal layer in contact with the metal oxide layer and comprising: Au and Pt.

In another aspect, the present invention provides a novel chemical sensor platform, comprising:
(a) an oxidized silicon membrane, comprising a silicon (Si) layer and a silicon oxide ($SiO_2$) layer, wherein the $SiO_2$ layer is located on top of the silicon layer and, comprises: a plurality of separate sensor areas;
(b) at least one heating element in contact with the $SiO_2$ layer and located near at least one edge of each sensor area;
(c) a plurality of pairs of electrical leads, each in contact with the $SiO_2$ layer, wherein 1 pair of electrical leads is at least partly located on each of the separate sensor areas;
(d) a plurality of metal oxide layers, wherein 1 metal oxide layer is located on each of the plurality of sensor areas and is in contact with at least a part of the pair of electrical leads located on the same area; and,
(e) a plurality of bimetal layers, wherein 1 bimetal layer is located in each sensor area and is in contact with the metal oxide layer in that area, wherein the bimetal layer, comprises: Au and Pd.

In another aspect, the present invention provides a novel chemical sensor platform, comprising:
(a) an oxidized silicon membrane, comprising a silicon (Si) layer and a silicon oxide ($SiO_2$) layer, wherein the $SiO_2$ layer is located on top of the silicon layer and, comprises: a plurality of separate sensor areas;
(b) at least one heating element in contact with the $SiO_2$ layer and located near at least one edge of each sensor area;
(c) a plurality of pairs of electrical leads, each in contact with the $SiO_2$ layer, wherein 1 pair of electrical leads is at least partly located on each of the separate sensor areas;
(d) a plurality of metal oxide layers, wherein 1 metal oxide layer is located on each of the plurality of sensor areas and is in contact with at least a part of the pair of electrical leads located on the same area; and,
(e) a plurality of bimetal layers, wherein 1 bimetal layer is located in each sensor area and is in contact with the metal oxide layer in that area, wherein the bimetal layer, comprises: Au and Pt.

In another aspect, in the chemical sensor platform there are 4 separate sensor areas, 1 heating element, 4 pairs of electrical leads, 4 metal oxide layers, and 4 bimetal layers.

In another aspect, in the chemical sensor platform there are 4 separate sensor areas, 1 Pt heating element, 4 pairs of Pt electrical leads, 4 $SnO_2$ (metal oxide) layers, and 4 bimetal layers.

In another aspect, in the chemical sensor platform there are 4 separate sensor areas, 1 Pt heating element, 4 pairs of Pt electrical leads, 4 SnO$_2$ (metal oxide) layers, 4 bimetal layers, and 4 Si/SiO$_2$ connectors.

In another aspect, in the chemical sensor platform there are 4 separate sensor areas, 1 Pt heating element, 4 pairs of Pt electrical leads, 4 SnO$_2$ (metal oxide) layers, 4 bimetal layers, and 4 SiO$_2$/Si/SiO$_2$ connectors.

In another aspect, in the chemical sensor platform there are 4 separate sensor areas, 1 Pt/Ti (Ti being the $2^{nd}$ material) heating element, 4 pairs of Pt/Ti (Ti being the $2^{nd}$ material) electrical leads, 4 SnO$_2$ (metal oxide) layers, and 4 bimetal layers.

In another aspect, in the chemical sensor platform there are 4 separate sensor areas, 1 Pt/Ti (Ti being the $2^{nd}$ material) heating element, 4 pairs of Pt/Ti (Ti being the $2^{nd}$ material) electrical leads, 4 SnO$_2$ (metal oxide) layers, 4 bimetal layers, and 4 Si/SiO$_2$ connectors.

In another aspect, in the chemical sensor platform there are 4 separate sensor areas, 1 Pt/Ti (Ti being the $2^{nd}$ material) heating element, 4 pairs of Pt/Ti (Ti being the $2^{nd}$ material) electrical leads, 4 SnO$_2$ (metal oxide) layers, 4 bimetal layers, and 4 SiO$_2$/Si/SiO$_2$ connectors.

The bimetal layer being in contact with the metal oxide layer "dopes" the metal oxide layer. Dopes or dopant refers to the surface modification of the metal oxide layer (e.g., SnO$_2$) by the bimetal layer.

Membrane refers to a Si/SiO$_2$ wafer that is typically formed from an oxidized silicon wafer (SiO$_2$/Si/SiO$_2$ layers). The membrane is formed by removing one of the SiO$_2$ layers and a substantial portion of the Si layer. Typically, part of the original wafer (SiO$_2$/Si/SiO$_2$) is left to serve as connectors for the membrane.

In another aspect, the membrane (in the sensor or platform), further comprises: a plurality of insulating connectors. In another aspect, the membrane (in the sensor or platform), further comprises: a plurality of Si/SiO$_2$ connectors. In another aspect, the membrane (in the sensor or platform), further comprises: 4 Si/SiO$_2$ connectors. The Si/SiO$_2$ connectors are typically the remainder of an oxidized silicon wafer. In another aspect, the Si/SiO$_2$ connectors are thicker than the Si/SiO$_2$ membrane. In another aspect, the Si/SiO$_2$ connectors, further comprise a SiO$_2$ layer on the bottom (e.g., SiO$_2$/Si/SiO$_2$). The SiO$_2$/Si/SiO$_2$ can be an unmodified portion of an oxidized silicon wafer that was used to form the membrane.

In another aspect, the sensor is square and, further comprises: 4 Si/SiO$_2$ connectors (one at each corner). In another aspect, the sensor is square and, further comprises: 4 SiO$_2$/Si/SiO$_2$ connectors (one at each corner).

In another aspect, the sensor platform is square and, further comprises: 4 Si/SiO$_2$ connectors (one at each corner). In another aspect, the sensor platform is square and, further comprises: 4 SiO$_2$/Si/SiO$_2$ connectors (one at each corner).

In another aspect, the thickness of the (or independently each) bimetal layer is about 0.5, 0.6, 0.7, 0.8 0.9, 1, 1.5, 2, 2.5, 3, 3.5, 4, 4.5, to 5 nm.

In another aspect, the molar ratio of Au:Pd in the bimetal layer is from 10:1 to 1:1 (91% Au/9% Pd to 50% Au/50% Pd). Additional examples include 9:1, 8:1, 7:1, 6:1, 5:1, 4:1, 3:1, and 2:1.

In another aspect, the molar ratio of Au:Pt in the bimetal layer is from 10:1 to 1:1 (91% Au/9% Pt to 50% Au/50% Pt). Additional examples include 9:1, 8:1, 7:1, 6:1, 5:1, 4:1, 3:1, and 2:1.

In another aspect, the Au and Pd are simultaneously deposited via sputtering.

In another aspect, the Au and Pt are simultaneously deposited via sputtering.

In another aspect, the (or independently each) metal oxide is selected from: SnO$_2$, ZnO, V$_2$O$_5$, WO$_3$, TiO$_2$, Al$_2$O$_3$, and Fe$_2$O$_3$. In another aspect, the (or each) metal oxide is SnO$_2$.

In another aspect, the (or independently each) metal oxide layer is about 5, 10, 15, 20, 25, 30, 35, 40, 45, 50, 55, 60, 65, 70, 75, 80, 85, 90, 95, to 100 nm thick. In another aspect, the (or independently each) metal oxide layer is about 5 to 40 nm thick.

In another aspect, the (or independently each) heating element, comprises: a $1^{st}$ material selected from Pt, Au, and poly-silicon. In another aspect, the (or independently each) heating element, comprises: Pt.

In another aspect, the (or independently each) heating element is about 50, 100, 150, 200, 250, 300, 350, 400, 450, 500, 550, 600, 650, 700, 750, 800, 850, 900, 950 to 1,000 nm thick. In another aspect, the (or independently each) heating element is about 300 nm thick.

In another aspect, the (or independently each) heating element, further comprises: a $2^{nd}$ material layer sandwiched between the SiO$_2$ layer and the $1^{st}$ material layer. In another aspect, the (or independently each) $2^{nd}$ material layer, comprises: a metal selected from Ti and Cr. In another aspect, the (or independently each) $2^{nd}$ material layer, comprises: Ti. In another aspect, the (or independently each) $2^{nd}$ material layer is about 1, 2, 3, 4, 5, 6, 7, 8, 9, to 10 nm thick. In another aspect, the (or independently each) $2^{nd}$ material layer is about 2 nm thick. In another aspect, the (or independently each) $2^{nd}$ material layer is about 5 nm thick.

In another aspect, the (or independently each) electrical leads, comprise: a $1^{st}$ metal layer selected from Pt and Au. In another aspect, the (or independently each) electrical leads, comprise: Pt. In another aspect, the (or independently each) electrical leads are about 50, 100, 150, 200, 250, 300, 350, 400, 450, 500, 550, 600, 650, 700, 750, 800, 850, 900, 950 to 1,000 nm thick. In another aspect, the (or independently each) electrical leads are about 300 nm thick.

In another aspect, the (or independently each) electrical leads, further comprise: a $2^{nd}$ metal layer sandwiched between the SiO$_2$ layer and the $1^{st}$ metal layer. In another aspect, the (or independently each) $2^{nd}$ metal layer, comprises: a metal selected from Ti and Cr. In another aspect, the $2^{nd}$ metal layer, comprises: Ti. In another aspect, the (or independently each) $2^{nd}$ metal layer is about 1, 2, 3, 4, 5, 6, 7, 8, 9, to 10 nm thick. In another aspect, the (or independently each) $2^{nd}$ metal layer is about 2 nm thick. In another aspect, the (or independently each) $2^{nd}$ metal layer is about 5 nm thick.

In the platform, the number of sensor areas can vary. Examples include 2, 3, 4, 5, 6, 7, 8, 9, 10, or more. The number of sensor areas determines the number of pairs of electrical leads, metal oxide layers, and bimetal layers. The number of heating elements is independent of the number of sensor areas. For example, one heating element can service more than one sensor area (e.g., 1 heating element for 4 sensor areas). Examples of the number of heating elements include 1, 2, 3, 4, 5, or more.

In another aspect, in the platform plurality is 4.

In another aspect, in the platform the number of sensor areas is 4.

In the chemical sensor/platform, the SiO$_2$ layer is typically polished. The sensor area is where at least part of a pair of electrical leads is located as well as the metal oxide and bimetal layers. The heating element is not in contact with the electrical leads, the metal oxide layer, or the bimetal layer but is located close enough to be able to heat the metal oxide and bimetal layers. The bimetal layer substantially if not entirely covers the exposed or top side of the metal oxide layer (and is typically not in contact with the SiO$_2$ layer).

In another aspect, the silicon layer in the membrane is about 5, 10, 15, 20, 25, 30, 35, 40, 45, 50, 55, 60, 65, 70, 75, 80, 85, 90, 95, to 100 μm thick. This is measured from the bottom of the SiO$_2$ layer to the bottom of the membrane. In another example, the silicon layer is about 50 μm thick.

In another aspect, the SiO$_2$ layer in the membrane is about 200, 250, 300, 350, to 400 nm thick. In another aspect, the SiO$_2$ layer is about 300 nm thick.

In another aspect, the thickness of the membrane is from 50, 100, 150, 200, 250, 300, 350, 400, 450 to 500 μm. In another aspect, the membrane thickness is 200 μm. In another aspect, the membrane thickness is 100 μm.

In another aspect, the present invention provides a novel device, comprising at least one sensor or sensor platform of the present invention.

Due to the small size of the present sensors/platforms and their rapid response times, the sensors/platforms can be used in devices, such as gas sensors. An example of such a device is a gas chromatograph (GC), in particular a portable GC. Thus, in another aspect, the present invention provides a novel GC, comprising: at least one sensor or platform of the present invention. In another aspect, the GC, further comprises: a suitable gas separating column (e.g., a polyethylene glycol column (e.g., a MXT-WAX column from Restek or a DB-WAX column from Agilent)). Other components that may be present include a heating over, a gas inlet, a pre-concentrator, a microprocessor (for running the GC components and communicating with an external device (e.g., a mobile device like a tablet or phone or a laptop/desktop computer).

EXAMPLES

The following examples are meant to illustrate, not limit, the present invention.

Example 1

A multi-sensor array system was developed in order to improve the performance of conventional metal-oxide detectors based on a single sensing element. Multiple electronically independent sensing elements significantly improve signal to noise ratio of the detector due to independence of their outputs without chemical exposure and their synchronized response when exposed. The detector has an integrated multi-sensory platform, with an array of four sensory elements and a modified transistor outline (TO) package.

The integrated multi-sensory platform (2.5×2.5×0.3 mm) was designed to control the operation of four sensory elements at high temperatures and provide synchronized multi-sensor analysis of gas samples. The proposed design provides high stability of the detector over a long period of time at elevated temperatures in the range between 200 and 400° C. The multi-sensory platform contains four pairs of platinum electrodes for four identical sensing elements and a platinum cross-shaped heater located on the suspended membrane (1.5×1.5×0.05 mm) at the center of the platform (FIG. 1(a)).

Figure 1B:
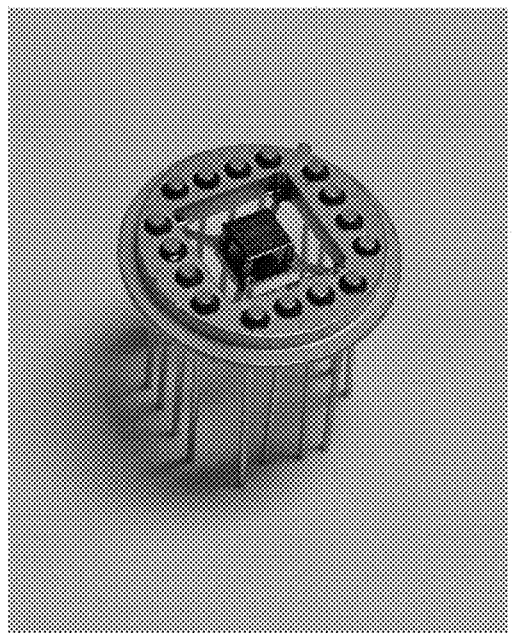
Figure 1C:
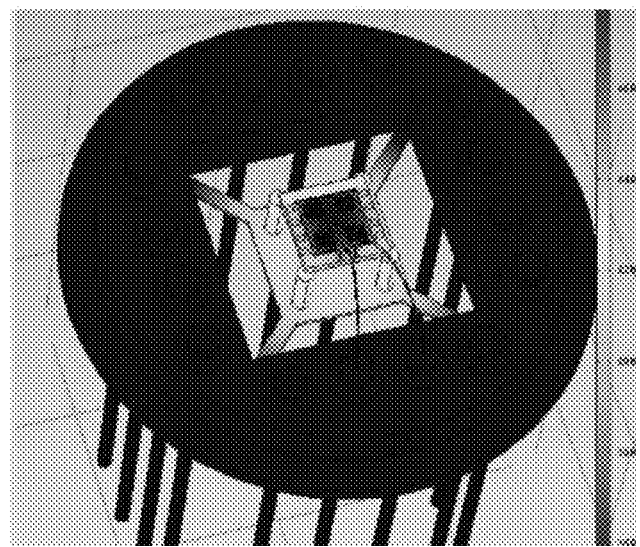
Figure 3:
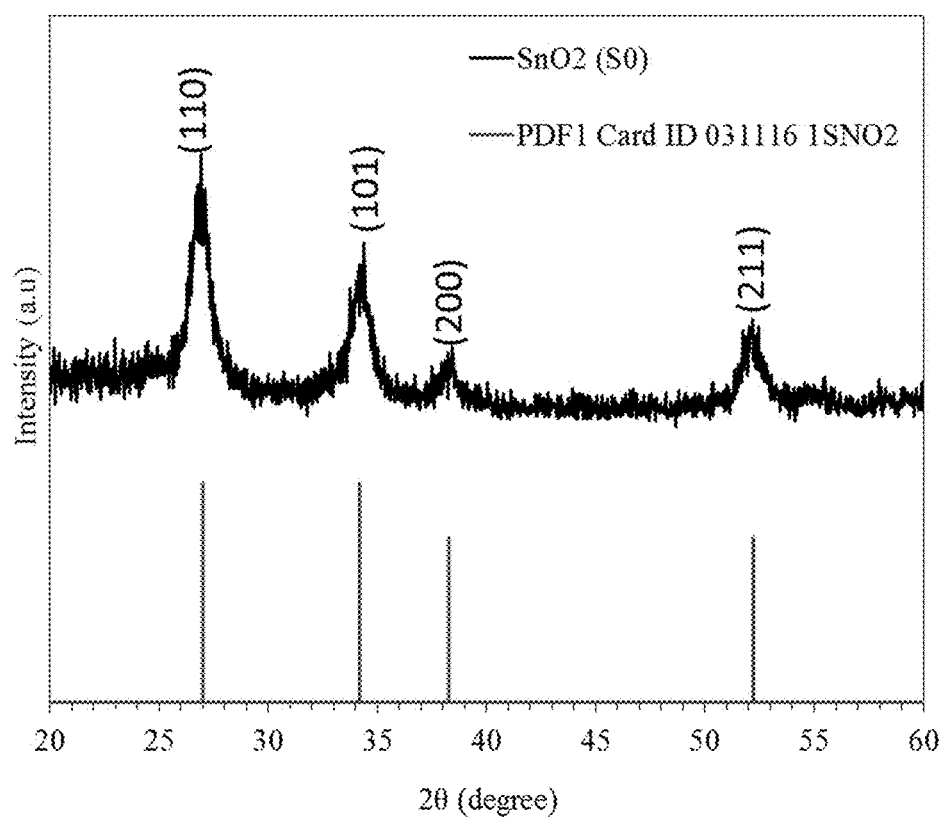
FIG. 3 is an XRD analysis of a $SnO_2$ thin film.

The contacts and the heater were simultaneously fabricated on a Si/SiO$_2$ (300/0.5 μm) substrate by using photolithographic (Suss Mask Aligner MA6/MA8) and magnetron sputtering technique (KJL PVD 75 Sputtering System) followed by a liftoff process. The total thickness of 300 nm+/−10 nm of the Pt contacts and the heater was verified by using a surface profilometer (KLA-Tencor Alpha-Step IQ). The membrane structure (a structure wherein the Si/SiO$_2$ substrate that is substantially isolated from the surrounding substrate) was fabricated by using reactive ion etching (RIE) and deep reactive ion etching (DRIE) techniques by utilizing MARCH RIE CS-1701 and Oxford PlasmaLab System 100 ICP 300 Deep RIE instruments, respectively. The membrane is connected to the main platform's base via small Si/SiO$_2$ connectors. The temperature insulation of the multi-sensory platform from the TO package was accomplished by suspending the platform on thin metal legs at the corners of the platform. The electrical connection between the multi-sensory platform and the TO package was formed by using a wire-bonding technique (FIG. 1b). The temperature characterization of the detector was first obtained by COMSOL™ 5.2 simulation (FIG. 1c) and then verified by real time data from thermal imaging machine (Quantum Focus Instruments (QFI) InfraScope). The detector demonstrated outstanding thermal properties, such as low temperature gradient across the sensing element in combination with low power consumption per sensing element (Ref. 32).

The $i^{th}$ sensor's individual response, $Y_i$, is defined as a ratio of $i^{th}$ sensor's resistance in ambient air to its resistance in presence of analytes such as benzene, toluene, ethylbenzene and o-xylene, as described by Eq. (1):

$$\text{Sensor's response, } Y_i = \frac{R_{i_{air}}}{R_{i_{gas}}} \qquad (1)$$

The integrated detector's response is defined as an encoding function for the topological connectivity of the array and the non-linear response domain of the sensors and their relative orthogonality relationships, F, from all 4 sensing elements (sensors) and time, t, given by Eq. (2).

$$\text{Detector's response} = F(Y_1 \ldots Y_4, t) \qquad (2)$$

In another aspect, $F(Y_1 \ldots Y_4, t)$ is the sum of the detector responses at a given time Four different types of tin oxide (SnO$_2$) based nanocomposite thin films were prepared and comparative analysis of its gas sensing performance was conducted (Table 2). A thin layer of SnO$_2$ (30 nm+/−2 nm) was first deposited over all four sensors S0-S1. During the SnO$_2$ sputtering, the deposition rate was kept constant at 0.6 A/s by applying 200 W RF power to a 4 inch tin oxide (SnO$_2$ 99.99%) target under 12 mTorr of Argon pressure. The SnO$_2$ surface of sensor S1 was then coated with 1.5 nm+/−0.2 nm of gold (Au 99.99%). Similarly, the SnO$_2$ surface of S2 sensor was coated with 1.5 nm+/−0.2 nm of palladium (Pd 99.95%). The Au and Pd depositions were performed by applying 50 W DC power to a 2-inch metal target under 5 mTorr of argon pressure. The deposition rates of Au and Pd remained constant at 1 A/s and 0.5 A/s, respectively, over the deposition process. The SnO$_2$ surface of sensor S3 was coated with a thin Au/Pd (90%-10%) alloy layer by simultaneous sputtering from both Au and Pd targets. The DC power for the Pd target was adjusted to 15 W in order to decrease the deposition rate of Pd down to 0.1 A/s and the power for the Au target was left at 50 W. The thickness of all the layers were monitored during the deposition process by using quartz crystal sensor (Inficon, Gold, 6 Mhz) and verified by surface profilometer (Alpha Step 500).

TABLE 2

Sensors' structure and composition as deposited

| Sensor # | Sensor's bulk material | Sensor's surface modification |
|---|---|---|
| S0 | $SnO_2$ (30 nm +/− 2 nm) | — |
| S1 | $SnO_2$ (30 nm +/− 2 nm) | Au (1.5 nm +/− .2 nm) |
| S2 | $SnO_2$ (30 nm +/− 2 nm) | Pd (1.5 nm +/− 0.2 nm) |
| S3 | $SnO_2$ (30 nm +/− 2 nm) | Au/Pd (90%-10%) (1.5 nm +/− .2 nm) |

The sensors S0-S3 had an amorphous structure after deposition. The synthesis of metal nanoparticles and the formation of $SnO_2$ nanocrystals from the amorphous layers was achieved via high-temperature calcination (annealing) process. The samples were calcined in a tube furnace (MTI) at 600° C. for 12 hours under a flow rate of 100 sccm (Standard Cubic Centimeters per Minute) of ultra-zero grade air (Air gas). During the heating and cooling stage of the calcination process, the furnace was pre-programmed for slow temperature ramping at the constant rate of 10° C. per minute. After the calcination process, the morphology of the samples S0-S3 was investigated by using scanning electron microscopy (SEM, Zeiss Supra 35), tunneling electron microscopy (TEM, JEOL, 100CX) and x-ray diffraction method (XRD, Thermo ARL model XTRA).

The morphology of the 30 nm $SnO_2$ layer (S0) was first investigated by SEM imaging technique. The SEM analysis revealed its porous and nano-crystalline structure with a uniform coating (FIG. 2a). In addition to high porosity of the sample, no high agglomeration of the nanocrystals was found. It is important to note that ultra-thin films with thickness less or equal to 30 nm have an advantage over the thick films due to the combination of high porosity and low agglomeration of nanocrystals (5-10 nm in diameter). This feature of ultra-thin films allowed for combining high sensitivity and fast response of the sensor at the same time. The size of $SnO_2$ crystal was further determined by TEM analysis to be in the range between 7 and 10 nm (FIG. 2b). High surface roughness of the sample S0 was demonstrated by using AFM analysis (FIG. 2c). The average roughness of the sample surface was found to be 6.7 nm.

Different types of crystal planes and average sizes of $SnO_2$ nanocrystals were finally characterized by X-ray diffractometer with Cu Kα (λ=1.5056 Å), operated at 30 kV and 20 mA. The X-Ray diffraction patterns for the sample were obtained with a scan rate of 0.02°/s over the range of 20°-60° (FIG. 2c). The peak with the highest intensity was obtained at 2θ=26.92°, which corresponds to the most stable (110) plane of the $SnO_2$. In addition, some other crystallographic planes (101), (200) and (211) with different structural and electronic configurations were formed at 2θ=34.22°, 38.21°, and 52.17°, respectively.

Finally, as a result of the XRD analysis, the average crystalline size among all the crystal planes of $SnO_2$ was calculated to be 7.9 nm from Scherrer formula (3):

$$D = \frac{K\lambda}{\beta \cos(\theta)}, \quad (3)$$

where K is the shape factor, which usually has a value 0.9, λ is the X-ray wavelength, θ the Bragg angle, and β gives the full width of the half maxima (FWHM).

Figure 4D:
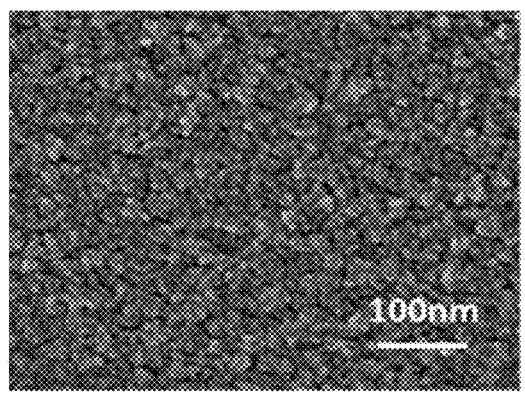
Figure 4E:
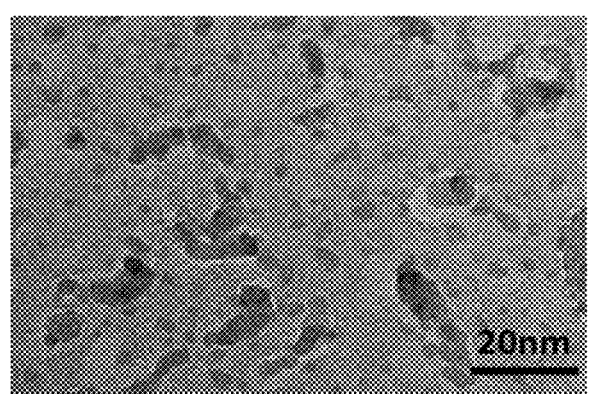
Figure 4F:
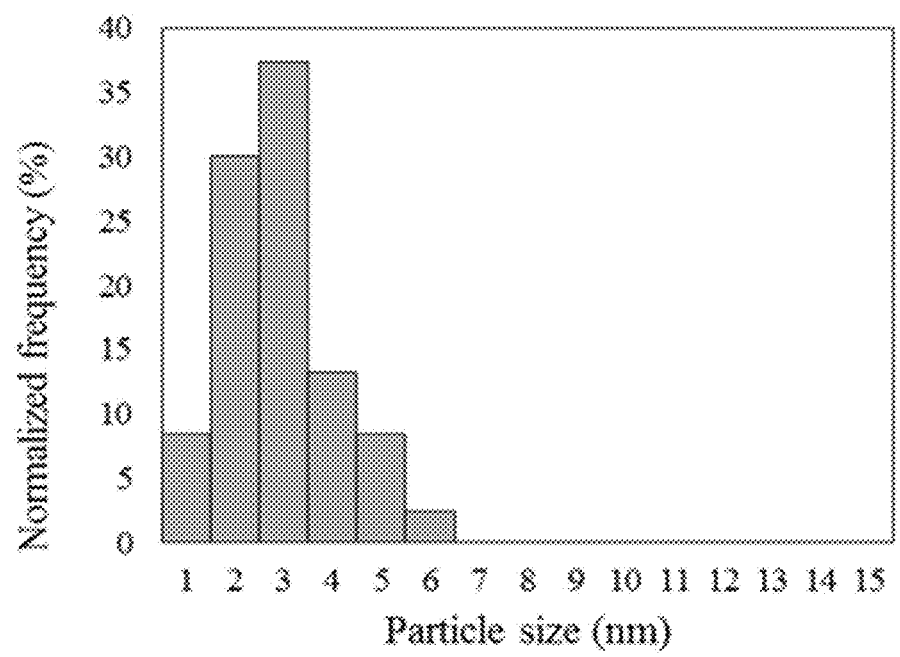

Morphologies of the samples S1-S3 were further investigated by using SEM and TEM (FIG. 4). SEM analysis of the sensors S1 and S3 demonstrated formation of spherical metal nanoclusters 5-10 nm in diameter on the surface of $SnO_2$ layer during the calcination process (FIGS. 4a, g). Also, the magnified surface images of the sensors S1 and S3 revealed an even distribution of metal nanoclusters across the sensing element and no agglomeration of metal nanoclusters was found. In the case of $SnO_2$ surface functionalized with Pd (S2), no visible metal nanoparticles were found by SEM analysis (FIG. 4d).

The overall SEM pictures of the samples S1-S3 demonstrated a uniform distribution of the sensing material across the sensing area. A more precise analysis of the surface morphology of the samples S1-S3 was then accomplished by utilizing a transmission electron microscope (TEM) (FIGS. 4b, e, and h). The higher resolution ability of the TEM analysis made it possible to describe the shape, average size, and particle agglomeration, as well as the density and size distribution of metal nanoclusters. Equal distributions of Au and Au/Pd spherical shape nanoparticles across the $SnO_2$ surface was found to be in a good agreement with SEM analysis for the samples S1 and S3, respectively, and no particle agglomeration into bigger clusters was found. Very small Pd nanoclusters of 2-4 nm in diameter were found while analyzing the sample S2 by TEM. According to TEM image (FIG. 4e), Pd nanoparticles have a tendency to agglomerate into bigger clusters, which makes it difficult to conduct a uniform surface modification of $SnO_2$ layer. Further analysis of the TEM images of the samples S1-S3 by utilizing LabVIEW vision module was used to determine the particle size distribution (FIG. 4c, f, and i) and the density of the nanoparticles per unit area (Table 3).

TABLE 3

Some important characteristics of the metal nanoparticles of the sensors S1-S3

| Sensor # | Nanoparticle size distribution | | Density of | Agglomeration of |
|---|---|---|---|---|
| | Mean (nm) | FWHM (nm) | Nanoparticles ($10^{10}/cm^2$) | nanoparticles? |
| Au@$SnO_2$ (S1) | 6.42 | 4.63 | 31 | No |
| Pd@$SnO_2$ (S2) | 2.68 | 2.72 | 141 | Yes |
| Au/Pd@$SnO_2$ (S3) | 7.63 | 4.21 | 25 | No |

Figure 5:
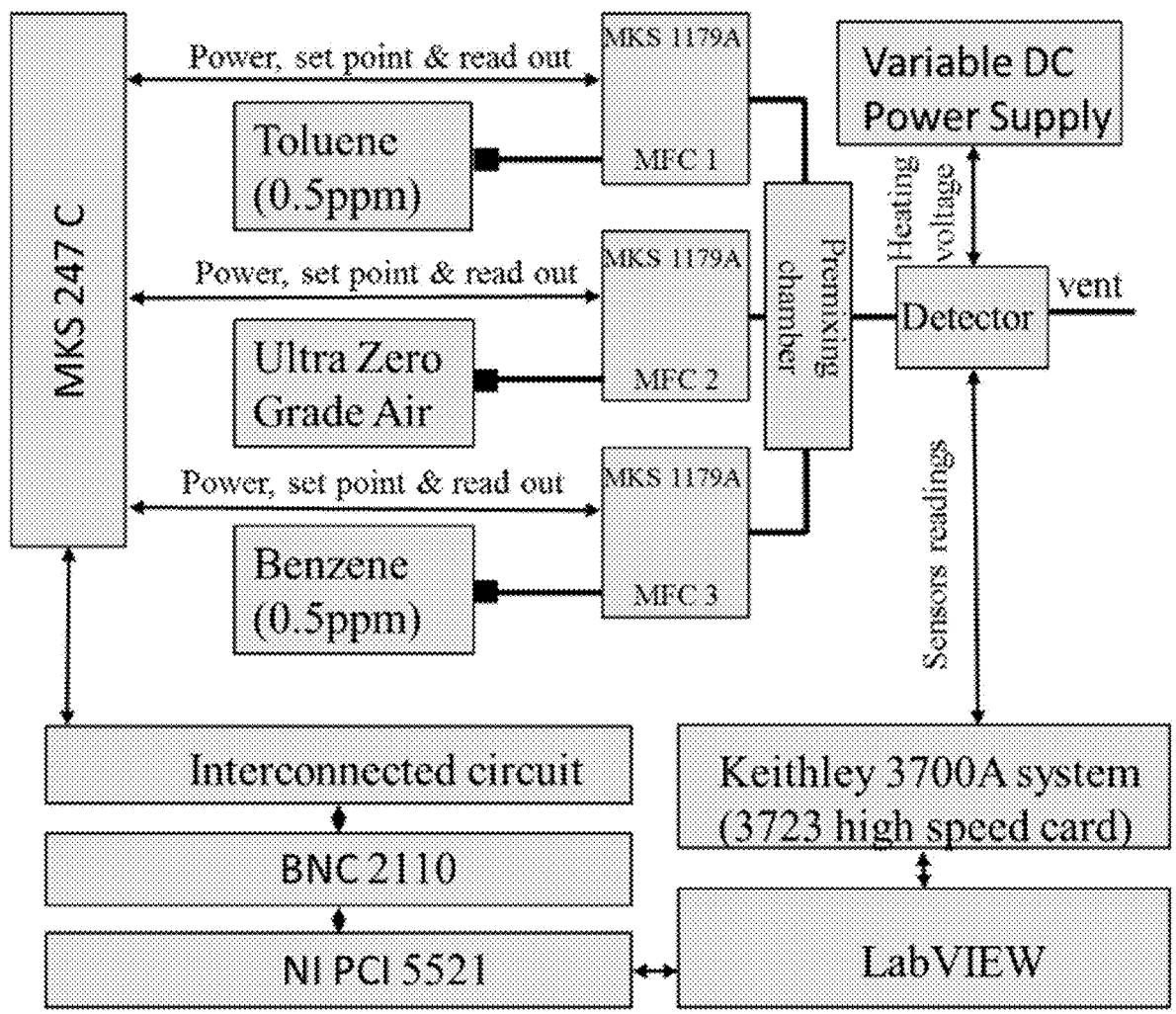
FIG. 5 is a schematic diagram of the multi-channel gas mixing system.

Multi-Channel Gas Mixing System:

A multi-channel gas mixing system was utilized for evaluation of sensors S0-S3. This system is capable of producing different gas concentrations of benzene and toluene in the range from 500 ppb down to 10 ppb by diluting commercially available pre-mixed gases of known concentrations (Benzene 0.5 ppm in 20% Oxygen, 80% Nitrogen and Toluene 0.5 ppm in 20% Oxygen, 80% Nitrogen) in Ultra Zero Grade Air. The flow rate from a single gas input was measured by a thermal mass flow meter and controlled by an integrated mass flow controller (MKS 1179A) with an accuracy of +/−1% within a full scale range from 0.2 to 10 sccm. Also, a gas pre-mixing chamber with a total volume of 5 cm³ was added to the system in order to produce a precise concentration of benzene and toluene down to sub ppm level. During the analysis, the total flow rate through the detector and detector's volume were kept constant at 10 sccm and 1 cm³ respectively. The multi-channel gas mixing system was controlled via LabVIEW software and NI PCI 6259 hardware (FIG. 5). The four probe DC resistance measurement of the sensing elements was conducted using a Keithley 3700A system switch/multimeter connected to a PC through LabVIEW interface. The resistance of each sensing element was measured with a sampling rate of 10 Hz. A similar data collection system was utilized for BTEX gas sample analysis with portable gas chromatograph (GC).

Figure 6A:
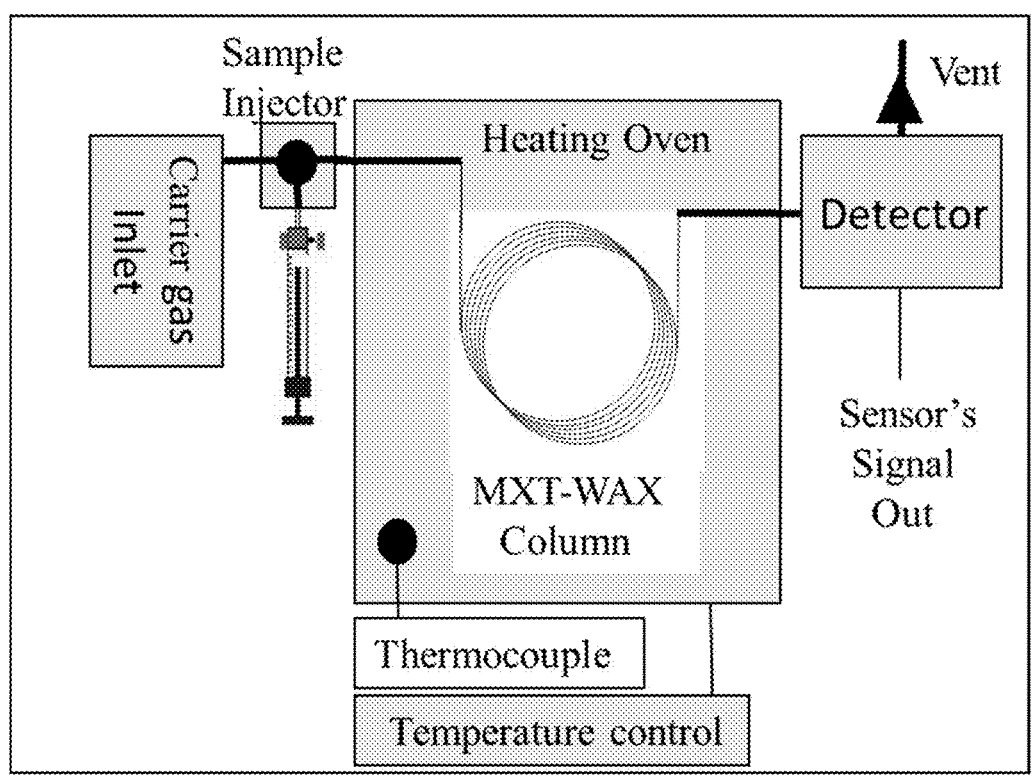
FIGS. 6A-C show a schematic diagram of a PAC R1120 portable GC (FIG. 6A), a schematic diagram of a table top GC (HP5890 GC) (FIG. 6B), and an image of the detector's chamber (FIG. 6C).
Figure 6B:
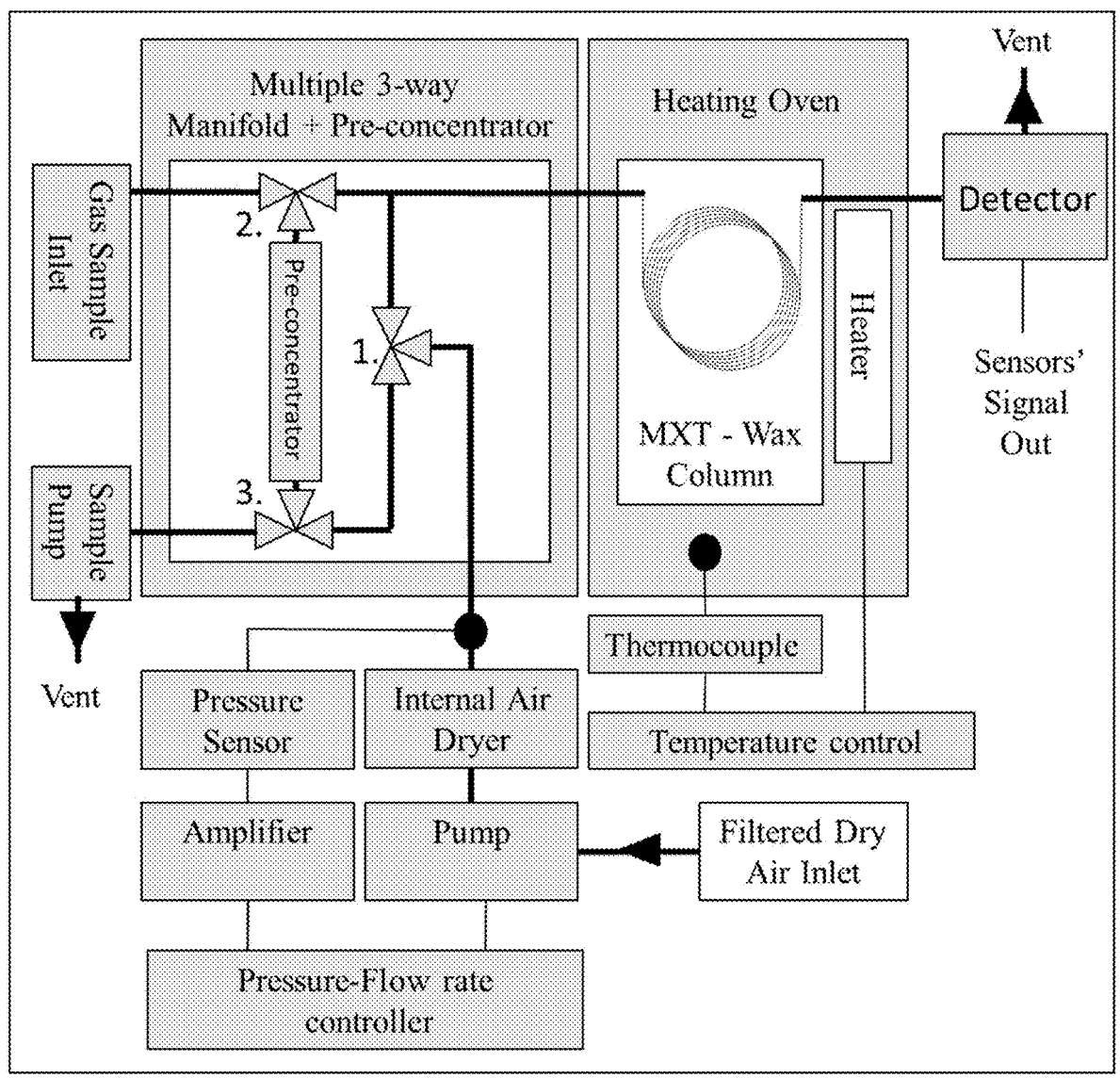
Figure 6C:
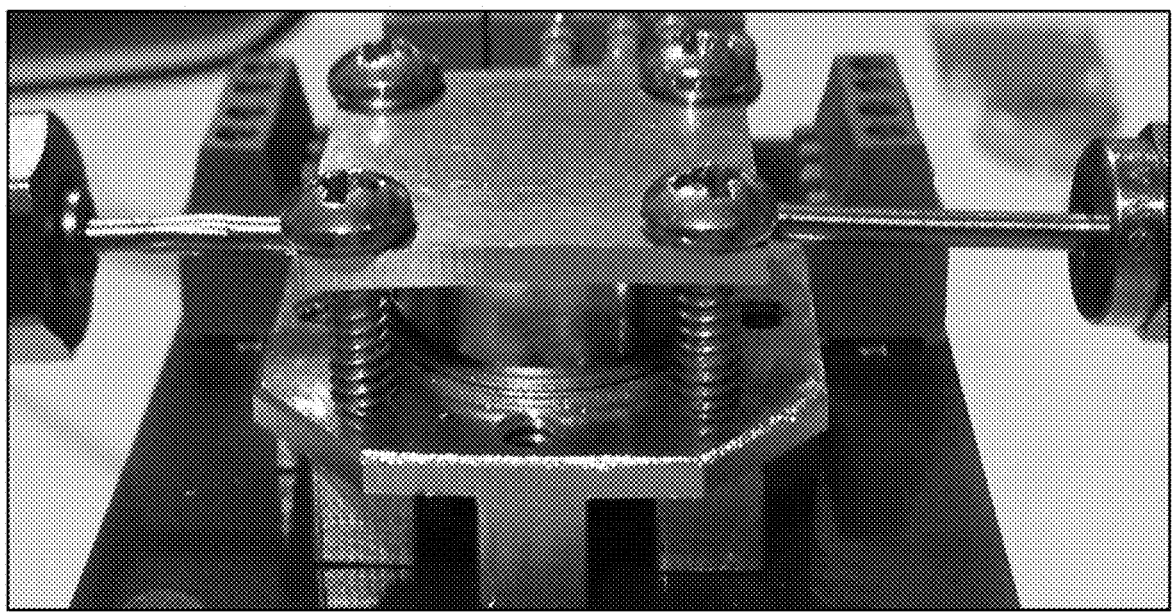

Portable GC Unit:

A portable GC analyzer PAC R1120 (FIG. 6a) was used in this testing procedure. The GC unit was equipped with a MXT WAX (30 m) column with 0.53 mm (ID) and 2 μm (df) from Restek under fixed operational conditions: flow rate of 14 sccm of clean dry air and constant column temperature of 55° C. The GC operating cycle includes three steps: sampling, gas mixture separation, and detection. During the first step, the gas sample was injected into the system. The gas samples for the analysis were prepared from premixed BTEX (Benzene 5.2 ppm, Toluene 5.2 ppm, Ethylbenzene 5.2 ppm and O-Xylene 5.2 ppm) calibration gas bottle by diluting the known concentration into ultra-zero grade air by using gas sample bags (SamplePro FlexFilm, 1L). The sample volume of 100 mL was kept constant for all the experiments. It is important to note that in contrast to the straight gas sample injection into the GC column when utilizing a classical table top GC (FIG. 6b), the portable GC unit was equipped with a sample pre-concentrator. The BTEX components are absorbed on the surface of the pre-concentrator under room temperature during the sampling step and then instantly injected into the GC column by rapidly increasing the temperature of the pre-concentrator. During the second step, the gas mixture was separated inside the capillary column by the differences in molecular weight, polarity, and chemical composition. Finally, the detection of gas components was performed by the detector inside a small volume of 1 $mL^3$ (FIG. 6c). After the analysis, the purging and cleaning circle was applied to the systems to remove the leftover contaminants.

Testing-Operational Temperature and Sensitivity Measurements:

After the sensors were fabricated and fully characterized, a series of experiments was conducted in order to evaluate their performance. A comparative analysis of the sensors was accomplished by utilizing a multi-channel gas mixing system for sensor exposure to different concentration of benzene (12.5-500 ppb) and toluene (12.5-500 ppb). Some important sensors' characteristics were obtained, such as: the optimal operational temperature, response value ($R_{air}/R_{gas}$), time of response ($T_{90}$), as well as the detection limit upon steady state exposure to low concentrations of benzene and toluene. Operation of sensors in different humidity levels was also studied.

Figure 7A:
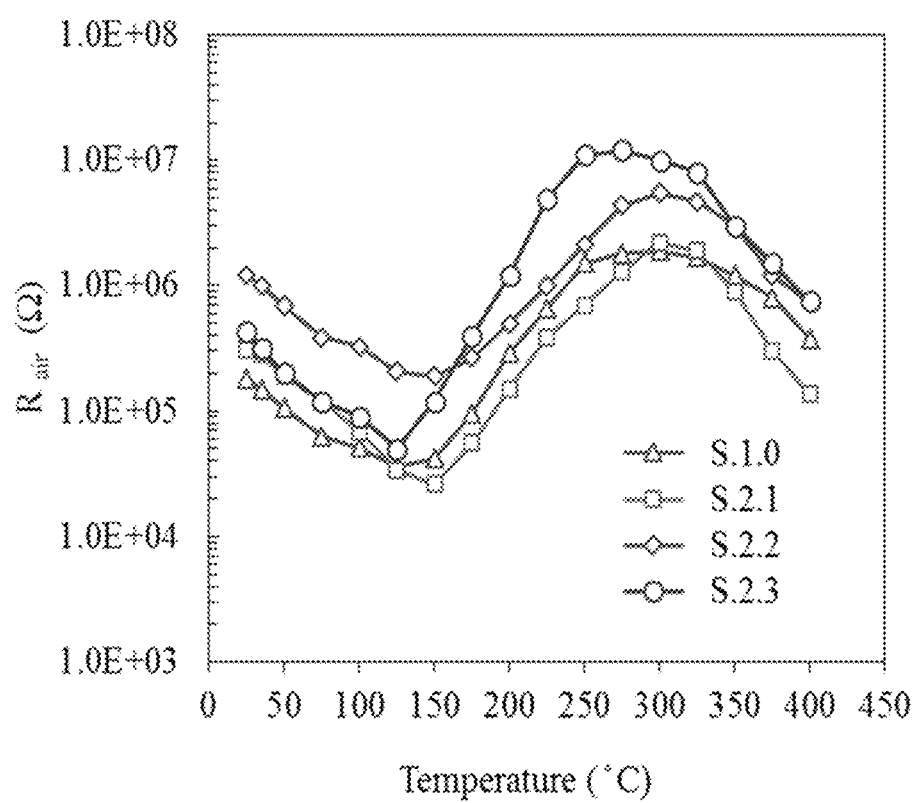
FIGS. 7A-C show the baseline resistance of the sensors S0-S3 in ultra-zero grade air (FIG. 7A), the corresponding resistance of sensors S0-S3 in the presence of 0.5 ppm of benzene (FIG. 7B), and the calculated response of sensors S0-S3 to 0.5 ppm of benzene over the temperature range from 25 to 400° C.
Figure 7B:
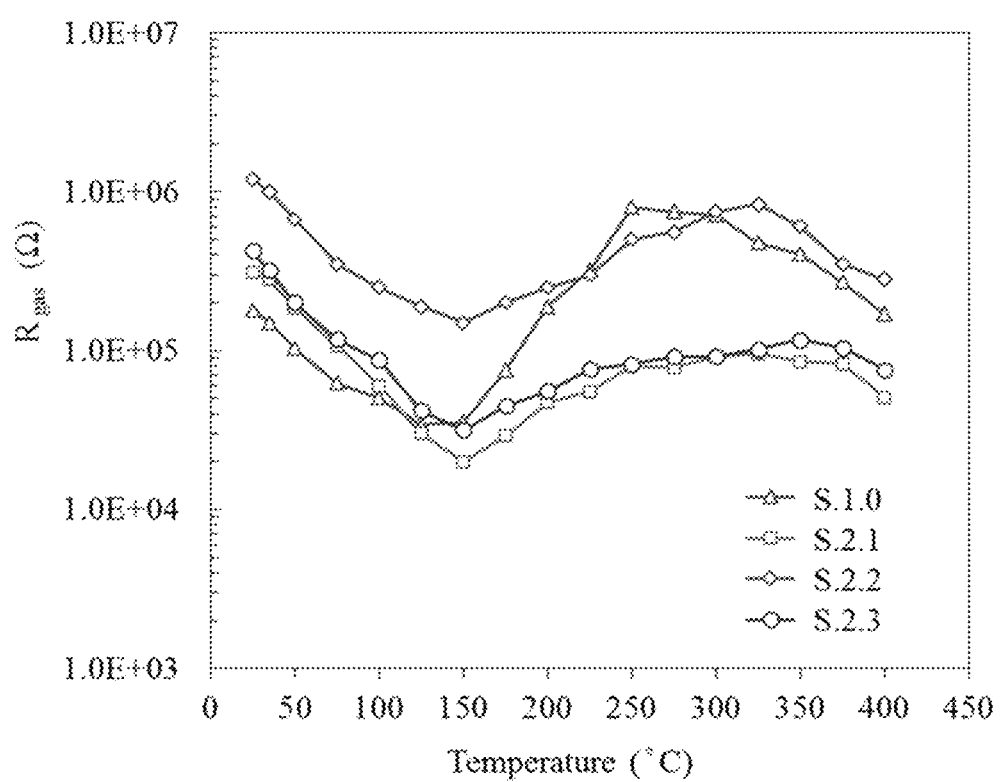
Figure 7C:
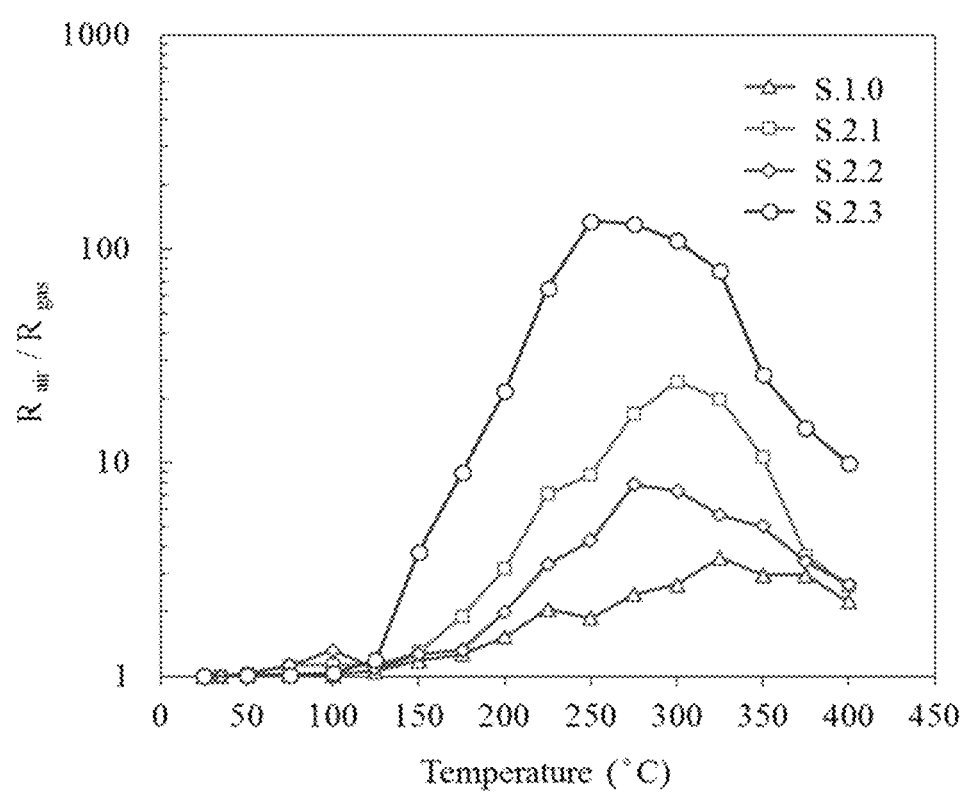

The optimum operational temperature of the sensors S0-S3 for detection of low concentrations of benzene and toluene was found by using a multi-channel gas mixing system. During the experiment, the baseline resistance was measured in ultra-zero grade air (FIG. 7a) under different temperature conditions in a range from 25 to 400° C. and the change of the sensor's resistance was then recorded upon steady state exposure to 0.5 ppm of benzene (FIG. 7b). The sensors' response ($R_{air}/R_{gas}$) was then calculated for each temperature condition and the optimum temperature with a corresponding maximum sensor performance was found for all four sensors (S0-S3) (FIG. 7c). It was found that when the target gas was switched from benzene to toluene of the same concentration, the same result for the optimum operating temperature was obtained for all the sensors.

The pure $SnO_2$ sensor demonstrated very poor sensitivity and high operational temperature of 325° C. Surface modification of the $SnO_2$ layer with gold or palladium nanoparticles slightly decreased the operational temperature of sensors S1 and S2 to 300° C. and 275° C., respectively. At the same time, a significant increase in sensitivity of nanoparticle-functionalized sensors was observed in comparison with the pure $SnO_2$ sensor (S0). It is important to notice that the sensor S2 functionalized with Pd demonstrated higher baseline resistance compared to the sensor S1 functionalized with Au nanoparticles. Such a dramatic difference under identical conditions reveals a potentially different mechanism of interaction between $SnO_2$ nanocrystals and palladium nanoparticles compared to $SnO_2$ interaction with nanoscale gold. The highest baseline resistance as well as the highest response was observed for the $SnO_2$ functionalized with bimetal Au/Pd alloy nanoparticles (S3). The lowest operational temperature of 250° C. was also observed for the same sensor S3.

Figure 8A:
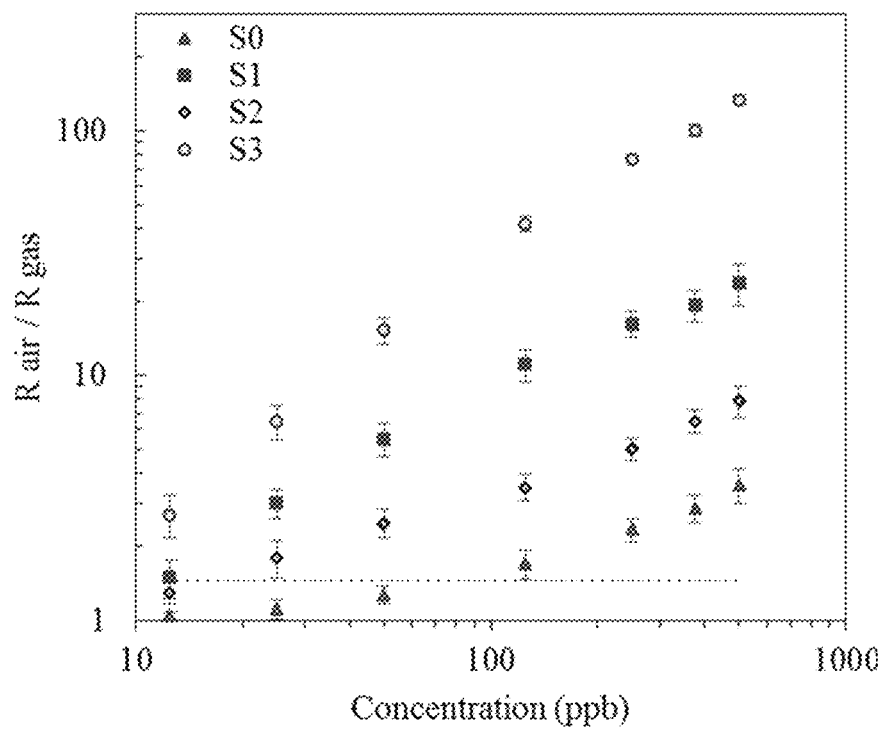
FIGS. 8A-B show sensor responses to different concentrations of benzene (FIG. 8A) and toluene (FIG. 8B) in a range between 12.5 and 500 ppb. The horizontal dashed line shows the threshold.
Figure 8B:
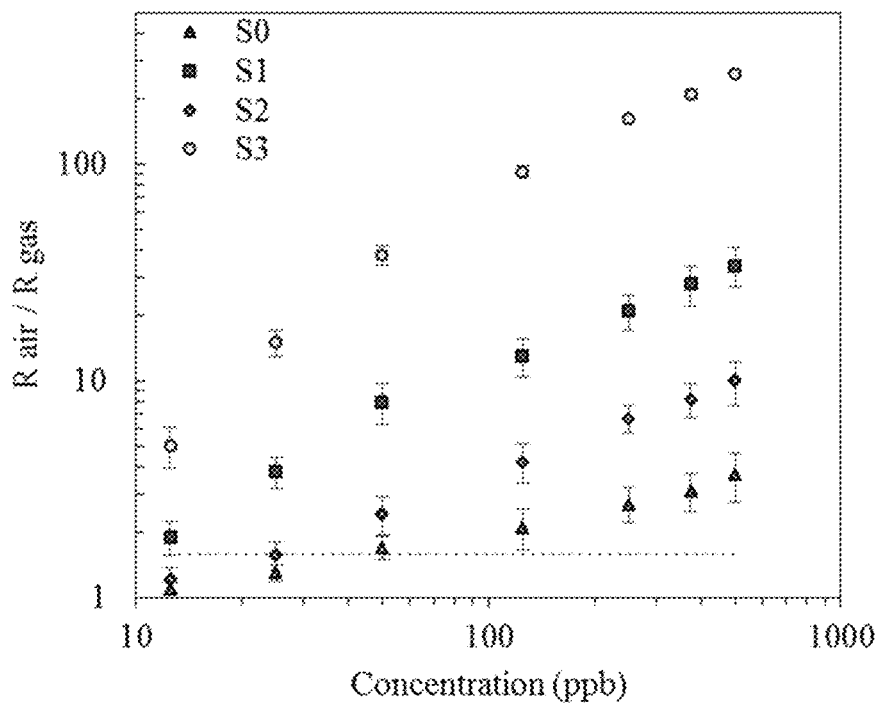

After the optimum operational temperature was determined, the sensors' responses to different concentrations of benzene and toluene in a range between 12.5 and 500 ppb and the sensors' baselines were monitored over a period of two weeks (FIGS. 8 a,b). All of the sensors demonstrated linear behavior upon exposure to lower concentrations (10-100 ppb) of benzene and toluene and slightly saturated behavior in case of higher concentrations (>100 ppb). It was found that functionalization of sensors with metal nanoparticles (Au, Pd, and Au/Pd) increases the sensitivity of sensors S1-S3 compared to the bare $SnO_2$ sensor S0. Sensor S3 demonstrated the highest sensitivity toward the low concentrations of benzene and toluene.

The minimum limit of detection (LOD) for benzene and toluene with a confidence level of 99.7% was determined by analyzing the drift in the sensor's baseline and the sensor's response over the period of two weeks. In this analysis, the normal distribution function was used to find the average value and the standard deviation of the baseline over time and the variations in sensors' response over time for multiple identical exposures. A low detection limit is defined as minimum measurable signal exceeding the threshold. The threshold is equal to the mean value of noise plus 3 standard deviations of the noise. The distance of 3 standard deviations from the mean value corresponds to 99.7% of the area under the normal distribution curve. Hence, the choice of parameters will assure that the signal can be distinguished from noise with the 99.7% probability. In FIG. 8, the horizontal dashed line shows the level of threshold. All the points above the threshold can be detected with 99.7% probability or higher.

Time of Response:

Another important parameter for sensor characterization, time of response ($T_{90}$), was found upon time-controllable exposure of the sensors to 500 ppb of benzene (Table 4). During the experiment, an instant change in gas concentration was achieved by minimizing the detector volume down to 0.5 $cm^3$ and utilizing a premixed benzene bottle with a concentration of 500 ppb. It was found that the response time was improved significantly by decorating the surface of $SnO_2$ with metal nanoparticles. The fastest response demonstrated was sensor S3, functionalized with bimetal (Au/Pd) nanoparticles. Sensor S2 modified with Pd nanoparticles demonstrated faster response time compared to the sensor S1 modified with gold nanoclusters.

TABLE 4

Operational temperature, time of response and limit of detection of sensors S0-S3 relevant to benzene and toluene.

| Sensor # | Benzene | | | Toluene | | |
|---|---|---|---|---|---|---|
| | Operational Temp (° C.) | $T_{90}$ (sec) | LOD (ppb) | Operational Temp. (° C.) | $T_{90}$ (sec) | LOD (ppb) |
| S0 | 325 | 4.9 | 250 | 325 | 4.7 | 125 |
| S1 | 300 | 4.3 | 25 | 300 | 4.2 | 25 |
| S2 | 275 | 3.7 | 25 | 275 | 3.5 | 50 |
| S3 | 250 | 3.3 | <12.5 | 250 | 3.1 | <12.5 |

Figure 9A:
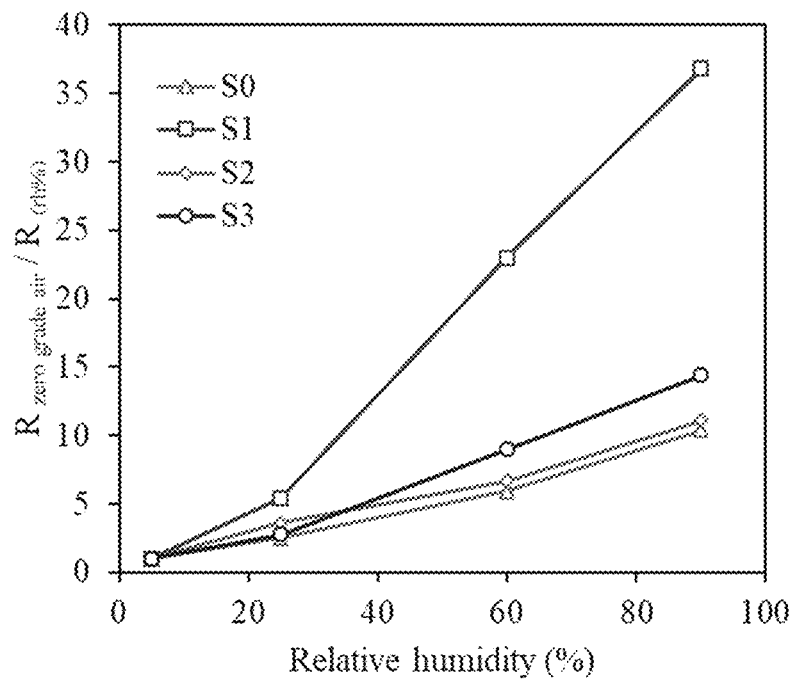
FIGS. 9A-B show the response of sensors S0-S3 to different relative humidity levels (FIG. 9A) and the response of the sensors S0-S3 to 0.5 ppb of benzene under different humidity conditions (FIG. 9B).
Figure 9B:
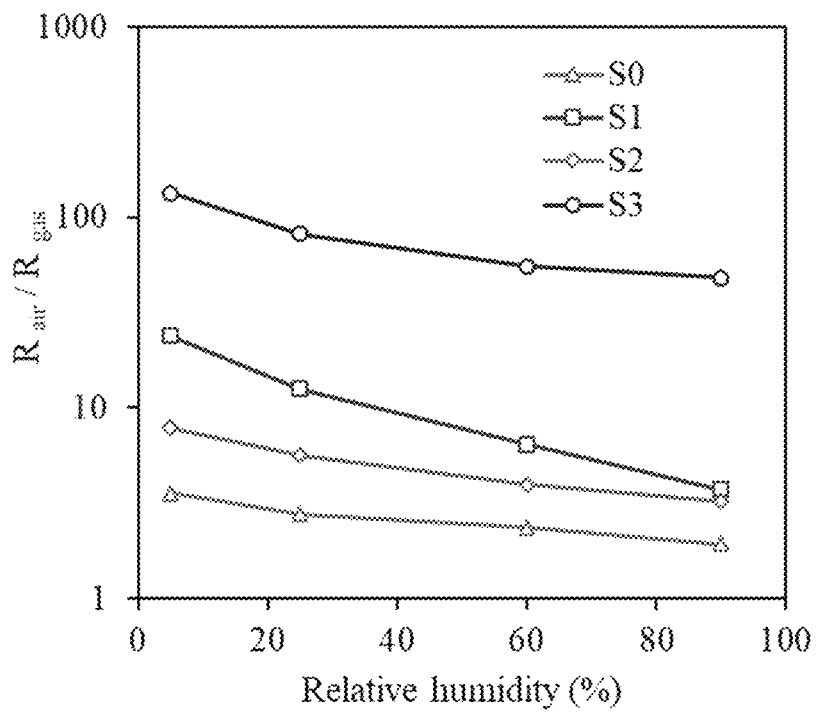

Humidity:

Also, a comparative analysis of the sensors' performance at different humidity levels as well as the response of sensors to 0.5 ppb of benzene under different humidity conditions was investigated. The baseline resistance of sensors S0-S3 was recorded upon exposing them to ultra-zero grade air and the corresponding humidity level inside the detector's chamber was found to be less than 5%. The response of each sensor upon increasing the relative humidity to 25, 60 and 90% was then calculated (FIG. 9a). It was found that all of the sensors are responsive to the humidity change. Sensor S1, modified with Au nanoparticles, demonstrated the highest drift in the sensor's baseline under high relative humidity conditions (40-90%) and a moderate baseline drift was recorded for sensors S0, S2 and S3. The responses of sensors S0-S3 upon exposure to 0.5 ppb of benzene were collected under different humidity conditions (FIG. 9b). It was demonstrated that the responses were affected by the humidity level. The highest (>6 times) change in response was found for sensor functionalized with Au nanoparticles (S1).

The comparative analysis of sensors S0-S3 in terms of their optimal operational temperature, time of response, lowest detection limit and performance under different humidity conditions revealed the superiority of sensor S3. This sensor, with bimetal Au/Pd nanoparticles, demonstrated the lowest operational temperature, the highest response to low concentrations of benzene and toluene, and the fastest response time, compared to the rest of the sensors (S0-S2). The sensor's signal was not highly affected by the change in relative humidity of the carrier gas and the sensitivity of the sensor stayed high even under 90% humidity level. Due to its superior properties, sensor S3 was further used for detection of ppb and sub-ppb level of BTEX components by utilizing a portable GC analyzer.

Figure 10A:
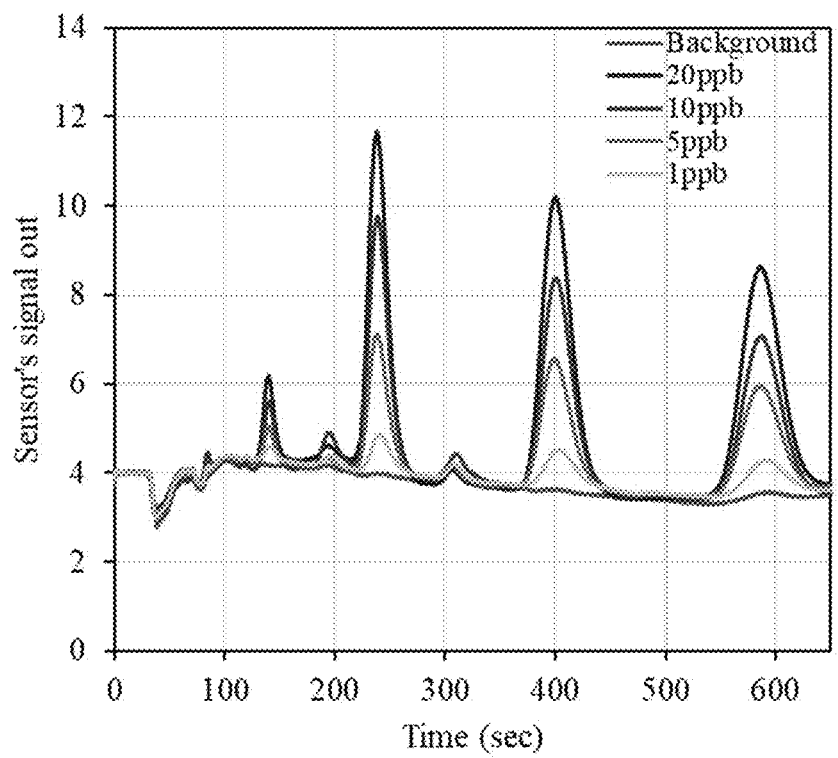
FIGS. 10A-C show gas chromatograms of different concentrations (1-20 ppb) of BTEX mixture (FIG. 10A), the detector's signal after the background was subtracted (FIG. 10B), and the calculated integrated detector's response to different concentrations of BTEX components (FIG. 10C).
Figure 10B:
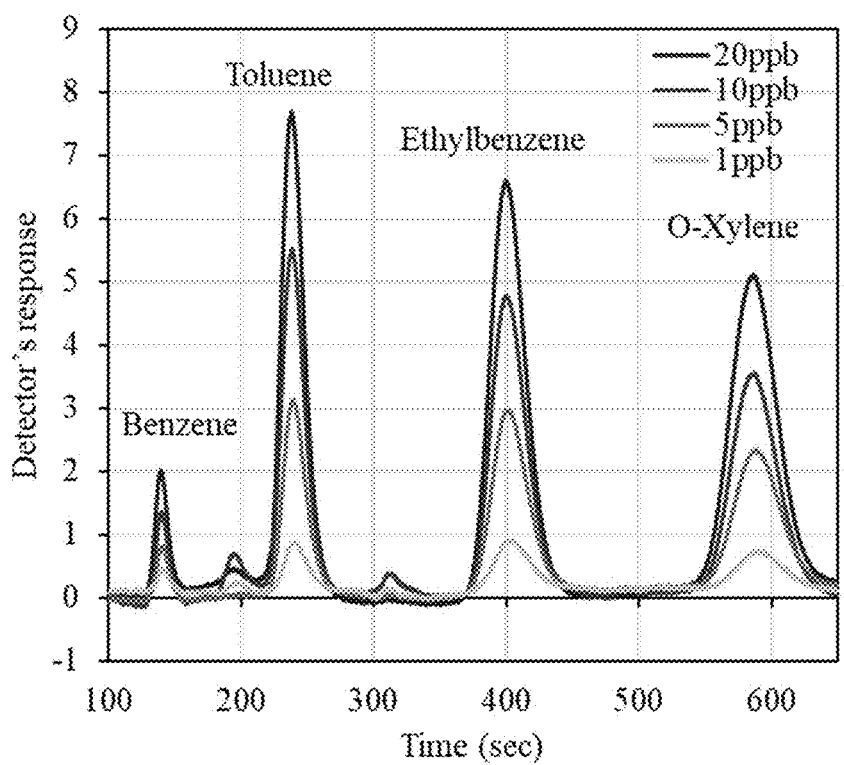
Figure 10C:
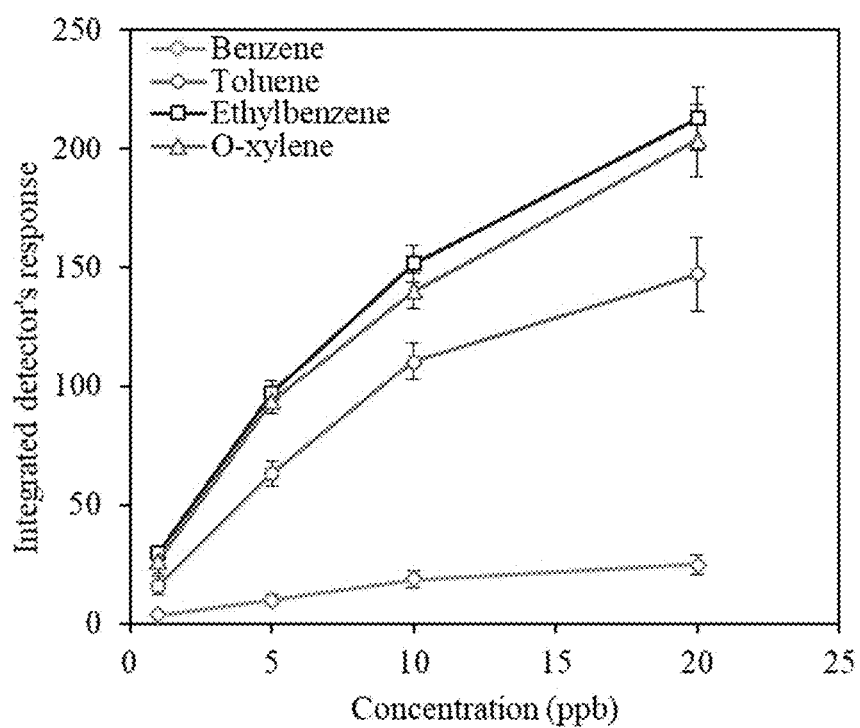

S3 Detection of PPB and Sub-PPB:

Sensor S3 demonstrated an ability to detect ppb and sub-ppb levels of BTEX traces in the air by using the PAC R1120 portable GC analyzer. The sensor performance was fully investigated over a two week period upon exposure to different concentrations of BTEX mixtures in the range between 20 and 0.5 ppb. It was found that the BTEX mixture can be separated by utilizing an MXT-WAX 30 m capillary column from Restek under constant temperature and flow rate of 55° C. and 14 sccm. The complete analysis of BTEX compounds was obtained within the time interval of 10.5 min. The four major peaks for the individual BTEX components are shown in the FIG. 10a. After the background signal of the detector was subtracted (FIG. 10b), the integrated detector's response was found for different concentrations of BTEX mixture (FIG. 10c). The integrated detector's response for detection of individual BTEX components was calculated by integrating the area under the curve over the time window for the gas of interest such as benzene, toluene, ethylbenzene and O-xylene.

Figure 11A:
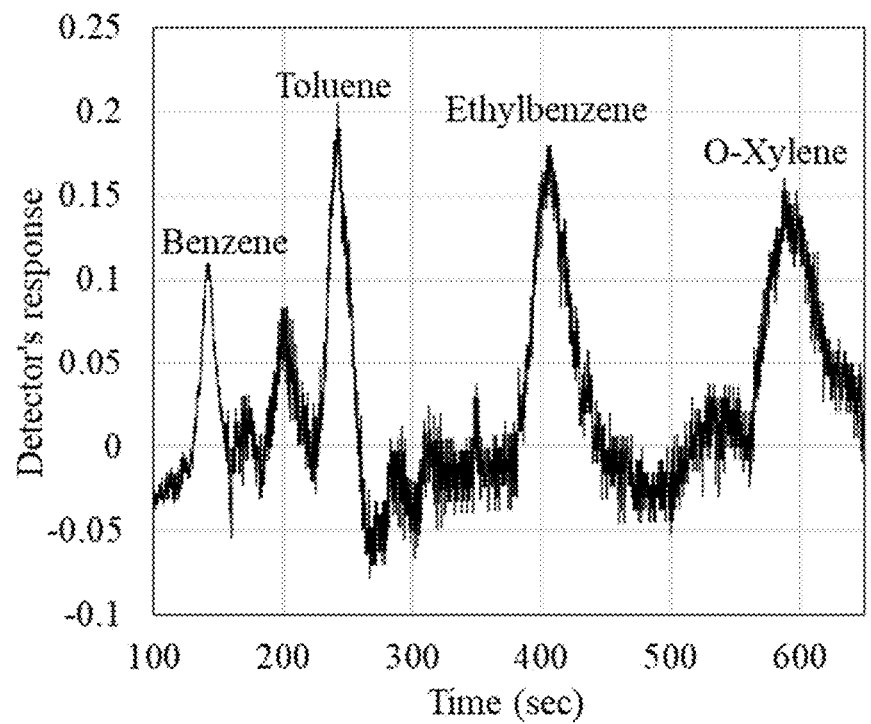
FIGS. 11A-B show gas chromatogram of 0.3 ppb of BTEX mixture (FIG. 11A) and integrated detector's response to 0.3 ppb of BTEX mixture and the GC background analysis (FIG. 11B).
Figure 11B:
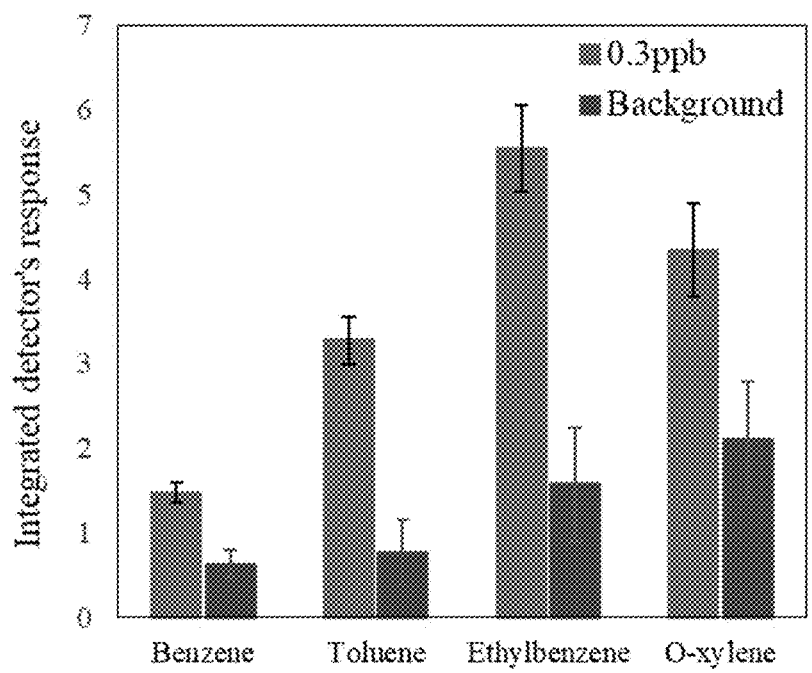

An additional analysis of ultra-low concentration of BTEX (0.3 ppb) demonstrated the sub-ppb detection capabilities of the detector (FIG. 11a). The background signal from the GC due to the leftover contamination of the system was recorded upon analyzing the zero grade air sample. It was found that the integrated detector's response to 0.3 ppb of BTEX was higher than the background signal of the portable GC for all the BTEX components with a confidence level of 99.7% (FIG. 11b). The sub-ppb level of detection of sensor S3 makes it possible to utilize it for real time indoor air quality monitoring. It is worth noting that the fast response and recovery time of the detector, upon exposure to reducing gases, substantially increases the GC selective ability of the device and improves the air sample analysis in the case of complex contaminated backgrounds or high humidity conditions.

A comparative analysis of sensing performance of bare $SnO_2$ sensor and $SnO_2$ functionalized with various metal nanoparticles was performed. The superiority of sensor functionalized with bimetal Au/Pd nanoparticles for detection of low concentrations of benzene and toluene was demonstrated experimentally. The combination of the extremely high catalytic activity of the sensor's surface and electronic interaction between the surface and the bulk allowed us to build a multisensory detector for air quality control and reach the sub-ppb level for detection of BTEX compounds in the indoor air by using portable GC analyzer.

REFERENCES

K. Harada, A. Hasegawa, C. Wei, K. Minamoto, Y. Noguchi, K. Hara, et al. A review of indoor air pollution and health problems from the viewpoint of environmental hygiene: Focusing on the studies of indoor air environment in Japan compared to those of foreign countries. *J. Health Sci.*, 56, (2010), 488-501. http://doi.org/10.1248/jhs.56.488

(2) O. Geiss, G. Giannopoulos, S. Tirendi, J. Barrero-Moreno, B. R. Larsen, D. Kotzias, The AIRMEX study—VOC measurements in public buildings and schools/kindergartens in eleven European cities: statistical analysis of the data, *Atmos. Environ.*, 45, (2011), 3676-3684. http://dx.doi.org/10.1016/ji.atmosenv.2011.04.037

(3) M. Sarkhosh, A. H. Mahvi, M. R. Zare, Y. Fakhri, H. R. Shamsolahi, Indoor contaminants from hardcopy devices: characteristics of VOCs in photocopy centers, *Atmos. Environ.*, 63, (2012), 307-312. http://dx.doi.org/10.1016/j.atmosenv.2012.09.058

(4) M. Derudi, S. Gelosa, A. Sliepcevich, A. Cattaneo, R. Rota, D. Cavallo, et al., Emissions of air pollutants from scented candles burning in a test chamber, *Atmos. Environ.*, 55, (2012), 257-262. http://dx.doi.org/10.1016/j.atmosenv.2012.03.027

(5) W. Ye, J. C. Little, D. Won, X. Zhang, Screening-level estimates of indoor exposure to volatile organic compounds emitted from building materials, *Build. Environ.*, 75, (2014), 58-66. http://dx.doi.org/10.1016/j.buildenv.2014.01.018

(6) Lui H, Wen S, Feng Y, Wang X, Bi X, Sheng G, et al. Indoor and outdoor carbonyl compounds and BTEX in the hospitals of Guangzhou, China. *Sci. Total Environ*, 368, (2006), 574-84.http://dx.doi.org/10.1016/j.scitotenv.2006.03.044

(7) I. Iarc, Overall evaluations of carcinogenicity: an uPdating of IARC monographs, IARC Monogr. Eval. Carcinog. Risk Chem. Hum., 7, (1987), 1-42. http://monographs.iarc.fr/ENG/Monographs/PDFs/

(8) K. Sexton, et al. Estimating volatile organic compound concentrations in selected microenvironments using time-activity and personal exposure data. *Journal of Toxicology and Environmental Health, Part A*, 70, (2007), 465-476. http://dx.doi.org/10.1080/15287390600870858

(9) S. K. Brown. Volatile organic pollutants in new and established buildings in Melbourne, *Indoor Air.* 12 (2002) 55-63.http://dx.doi.org/10.1034/j.1600-0668.2002.120107.x

(10) Critical appraisal of the setting and implementation of indoor exposure limits in the EU. Brussels: European Commission, Joint Research Centre; 2005.

(11) M. de Blas, M. Navazo, L. Alonso, N. Durana, J. Iza, Automatic on-line monitoring of atmospheric volatile organic compounds: Gas chromatography-mass spectrometry and gas chromatography-flame ionization detection as complementary systems, *Sci. Total Environ.*, 409 (2011), 5459-5469. http://dx.doi.org/10.1016/j.scitotenv.2011.08.072

(12) D. F. Cui, X. Chen, L. L. Zhang, H. Y. Cai, and H. Li, A micro gas chromatography column with a micro thermal conductivity detector for volatile organic compound analysis, *The Review of scientific instruments*, 84(2), (2013), 025001. http://dx.doi.org/10.1063/1.4789526

(13) A. Gonzalvez, S. Garrigues, M. de la Guardia, S. Armenta, The ways to the trace level analysis in infrared spectroscopy, *Anal. Methods*, 3, (2011), 43-52. http://dx.doi.org/10.1039/C0AY00437E

(14) J. Moreau, E. Rinnert, Fast identification and quantification of BTEX coupling by Raman spectrometry and chemometrics, *Analyst*, 140, (2015), 3535-3542. http://dx.doi.org/10.1039/C5AN00035A

(15) R. Volkamer, T. Etzkorn, A. Geyer, U. Platt, Correction of the oxygen interference with UV spectroscopic (DOAS) measurements of monocyclic aromatic hydrocarbons in the atmosphere, *Atmos. Environ.* 32, (1998), 3731-3747. http://dx.doi.org/10.1016/S1352-2310(98)00095-8

(16) H. Skov, A. Lindskog, F. Palmgren, C. S. Christensen, An overview of commonly used methods for measuring benzene in ambient air, *Atmos. Environ.*, 35(1), (2001), 141-148. http://dx.doi.org/10.1016/S1352-2310(00)00512-4

(17) F. Brilli, B. Gioli, P. Ciccioli, D. Zona, F. Loreto, I. A. Janssens, et al., Proton transfer reaction time-of-flight mass spectrometric (PTR-TOF-MS) determination of volatile organic compounds (VOCs) emitted from a biomass fire developed under stable nocturnal conditions, *Atmos. Environ.*, 97, (2014), 54-67. http://dx.doi.org/10.1016/j.atmosenv.2014.08.007

(18) L. Y. Sung, R. H. Shie, C. J. Lu, Locating sources of hazardous gas emissions using dual pollution rose plots and open path Fourier transform infrared spectroscopy, *J. Hazard. Mater.*, 265, (2014), 30-40. http://dx.doi.org/10.1016/j.jhazmat.2013.11.006

(19) C. Liaud, N. T. Nguyen, R. Nasreddine, S. Le Calvé, Experimental performances study of a transportable GC-PID and two thermo-desorption based methods coupled to FID and MS detection to assess BTEX exposure at sub-ppb level in air, *Talanta*, 127, (2014), 33-42. http://dx.doi.org/10.1016/j.talanta.2014.04.001

(20) E. Gallego, F. J. Roca, J. F. Perales, G. Sánchez, P. Esplugas, Characterization and determination of the odorous charge in the indoor air of a waste treatment facility through the evaluation of volatile organic compounds (VOCs) using TD-GC/MS, *Waste Management*, 32, (2012), 2469-2481. http://dx.doi.org/10.1016/j.wasman.2012.07.010

(21) M. Blas, M. Navazo, L. Alonso, N. Durana, J. Iza, Automatic on-line monitoring of atmospheric volatile organic compounds: Gas chromatography-mass spectrometry and gas chromatography-flame ionization detection as complementary systems, *Science of The Total Environment*, 409, (2011), 5459-5469. http://dx.doi.org/10.1016/j.scitotenv.2011.08.072

(22) S. Zimmermann, S. Wischhusen, J. Müller, Micro flame ionization detector and micro flame spectrometer, *Sens. Actuators B Chem*, 63(3), (2000), 159-166. http://dx.doi.org/10.1016/S0925-4005(00)00353-1

(23) R. Nasreddine, V. Person, C. A. Serra, S. Le Calve, Development of a novel portable miniaturized GC for near real-time low level detection of BTEX, *Sens. Actuators B Chem*, 224, (2016), 159-169. http://dx.doi.org/10.1016/j.snb.2015.09.077

(24) A. Garg, M. Akbar, E. Vejerano, S. Narayanan, L. Nazhandali, L. C. Marrb, M. Agaha, Zebra GC: A mini gas chromatography system for trace-level determination of hazardous air pollutants, *Sens. Actuators B Chem*, 212, (2015), 145-154. http://dx.doi.org/10.1016/j.snb.2014.12.136

(25) E. J. Staples, T. Matsuda, and S. Viswanathan, Real Time Environmental Screening of Air, Water and Soil Matrices Using a novel Field Portable GC/SAW System, *Asia Pacific Conference*, (1998).

(26) L. Meciarova, S. Vilcekova, M. Balintova, Measurement of VOCs with a Portable GC/SAW Detector, *Chemical engineering Transaction*, 40, (2014), 283-288. http://dx.doi.org/10.3303/CET1440048

(27) W. A. Groves, E. T. Zellers, G. C. Frye, Analyzing organic vapors in exhaled breath using a surface acoustic wave sensor array with preconcentration: selection and characterization of the preconcentrator adsorbent, *Anal. Chim. Acta*, 371, (1998), 131-143. http://dx.doi.org/10.1016/S0003-2670(98)00294-3

(28) M. Benz, L. Benz, S. V. Patel, High temperature mass detection using a carbon nanotube bilayer modified quartz crystal microbalance as a GC detector, *Anal. Chem.*, 87, (2015), 2779-2787. http://dx.doi.org/10.1021/ac504101a

(29) A. Kumar, J. Brunet, C. Varenne, A. Ndiaye, A. Pauly, M. Penza, et al., Tetra-tert-butyl copper phthalocyanine-based QCM sensor for toluene detection in air at room temperature, *Sens. Actuators B Chem.*, 210, (2015), 398-407. http://dx.doi.org/10.1016/j.snb.2015.01.010

(30) R. A. Iglesias, F. Tsow, R. Wang, E. S. Forzani and N. Tao, Hybrid Separation and Detection Device for Analysis of Benzene, Toluene, Ethylbenzene, and Xylenes in Complex Samples, *Anal. Chem.*, 81 (21), (2009), 8930-8935. http://dx.doi.org/10.1021/ac9015769

(31) S. Zampolli, I. Elmi, F. Mancarella, P. Betti, E. Dalcanale, G. C. Cardinali, M. Severi, Real-time monitoring of sub-ppb concentrations of aromatic volatiles with a MEMS-enabled miniaturized gas-chromatograph, *Sens. Actuators B Chem.*, 141, (2009), 322-328. http://dx.doi.org/10.1016/j.snb.2009.06.021

(32) A. Larin, P. Womble, and V. Dobrokhotov, Hybrid $SnO_2/TiO_2$ Nanocomposites for Selective Detection of Ultra-Low Hydrogen Sulfide Concentrations in Complex Backgrounds, *Sensors*, 16(9), (2016), 1373. http://dx.doi.org/10.3390/s16091373

Numerous modifications and variations of the present invention are possible in light of the above teachings. It is therefore to be understood that within the scope of the

What is claimed is:

1. A chemical sensor platform, comprising:
   (a) an oxidized silicon membrane, comprising a silicon (Si) layer and a silicon oxide ($SiO_2$) layer, wherein the $SiO_2$ layer is located on top of the silicon layer and, comprises: a plurality of separate sensor areas;
   (b) at least one heating element in contact with the $SiO_2$ layer and located near at least one edge of each sensor area;
   (c) a plurality of pairs of electrical leads, each in contact with the $SiO_2$ layer, wherein one pair of electrical leads is at least partly located on each of the separate sensor areas;
   (d) a plurality of metal oxide layers, wherein one metal oxide layer is located on each of the plurality of sensor areas and is in contact with at least a part of the pair of electrical leads located on the same area;
   (e) a plurality of bimetal layers, wherein one bimetal layer is located in each sensor area and is in contact with the metal oxide layer in that area, wherein the bimetal layer, comprises: Au and Pd or Au and Pt; and
   (f) a plurality of $Si/SiO_2$ connectors that are configured to provide membrane support and temperature insulation of the membrane.

2. The chemical sensor platform of claim 1, wherein the bimetal layers, comprise: Au and Pd.

3. The chemical sensor platform of claim 1, wherein the bimetal layers, comprise: Au and Pt.

4. The chemical sensor platform of claim 1, wherein the membrane, further comprises: 4 $Si/SiO_2$ connectors.

5. The chemical sensor platform of claim 1, wherein bimetal layer, comprises: Au and Pd and the molar ratio of Au to Pd is from 10:1 to 1:1.

6. The chemical sensor platform of claim 1, wherein bimetal layer, comprises: Au and Pd and the molar ratio of Au to Pd is about 9:1.

7. The chemical sensor platform of claim 1, wherein bimetal layer, comprises: Au and Pd and the molar ratio of Au to Pt is from 10:1 to 1:1.

8. The chemical sensor platform of claim 1, wherein bimetal layer, comprises: Au and Pd and the molar ratio of Au to Pt is about 9:1.

9. The chemical sensor platform of claim 1, wherein the metal oxide is $SnO_2$.

10. The chemical sensor platform of claim 1, wherein the at least one heating element, comprises: Pt.

11. The chemical sensor platform of claim 1, wherein the plurality of pairs of electrical leads, comprise: Pt.

12. The chemical sensor platform of claim 1, wherein there are 4 separate sensor areas, 1 heating element, 4 pairs of electrical leads, 4 metal oxide layers, and 4 bimetal layers.

13. The chemical sensor platform of claim 1, wherein there are 4 separate sensor areas, 1 Pt heating element, 4 pairs of Pt electrical leads, 4 $SnO_2$ layers, and 4 bimetal layers.

14. The chemical sensor platform of claim 1, wherein there are 4 separate sensor areas, 1 Pt heating element, 4 pairs of Pt electrical leads, 4 $SnO_2$ layers, 4 bimetal layers, and 4 $Si/SiO_2$ connectors.

15. The chemical sensor platform of claim 1, wherein there are 4 separate sensor areas, 1 Pt heating element, 4 pairs of Pt electrical leads, 4 $SnO_2$ layers, 4 bimetal layers, and 4 $SiO_2/Si/SiO_2$ connectors.

16. The chemical sensor platform of claim 1, wherein there are 4 separate sensor areas, 1 Pt/Ti heating element, 4 pairs of Pt/Ti electrical leads, 4 $SnO_2$ layers, and 4 bimetal layers.

17. The chemical sensor platform of claim 1, wherein there are 4 separate sensor areas, 1 Pt/Ti heating element, 4 pairs of Pt/Ti electrical leads, 4 $SnO_2$ layers, 4 bimetal layers, and 4 $Si/SiO_2$ connectors.

18. The chemical sensor platform of claim 1, wherein there are 4 separate sensor areas, 1 Pt/Ti heating element, 4 pairs of Pt/Ti electrical leads, 4 $SnO_2$ layers, 4 bimetal layers, and 4 $SiO_2/Si/SiO_2$ connectors.

19. The chemical sensor platform of claim 1, wherein there are 4 separate sensor areas, 1 Pt/Ti heating element, 4 pairs of Pt/Ti electrical leads, 4 $SnO_2$ layers, 4 bimetal layers comprising: Au and Pd, and 4 $SiO_2/Si/SiO_2$ connectors.

20. The chemical sensor platform of claim 1, wherein there are 4 separate sensor areas, 1 Pt/Ti heating element, 4 pairs of Pt/Ti electrical leads, 4 $SnO_2$ layers, 4 bimetal layers comprising Au and Pd, and 4 $SiO_2/Si/SiO_2$ connectors.

* * * * *